US009877781B2

(12) United States Patent
Grasse et al.

(10) Patent No.: US 9,877,781 B2
(45) Date of Patent: Jan. 30, 2018

(54) ELECTRODE CATHETER DEVICE WITH INDIFFERENT ELECTRODE FOR DIRECT CURRENT TISSUE THERAPIES

(75) Inventors: Martin M. Grasse, Boston, MA (US); Richard E. Stehr, Tucson, AZ (US); Israel A. Byrd, Richfield, MN (US); Lynn E. Gilmour, Savage, MN (US); D. Curtis Deno, Andover, MN (US); Troy T. Tegg, Elk River, MN (US); James V. Kauphusman, Champlin, MN (US); Saurav Paul, Shoreview, MN (US); Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 738 days.

(21) Appl. No.: 13/885,776

(22) PCT Filed: Nov. 18, 2011

(86) PCT No.: PCT/US2011/061475
§ 371 (c)(1),
(2), (4) Date: May 16, 2013

(87) PCT Pub. No.: WO2012/068505
PCT Pub. Date: May 24, 2012

(65) Prior Publication Data
US 2013/0338467 A1 Dec. 19, 2013

Related U.S. Application Data

(63) Continuation-in-part of application No. 12/982,675, filed on Dec. 30, 2010, which is a
(Continued)

(51) Int. Cl.
*A61N 1/00* (2006.01)
*A61B 5/04* (2006.01)
(Continued)

(52) U.S. Cl.
CPC .............. *A61B 18/16* (2013.01); *A61B 5/042* (2013.01); *A61B 18/1492* (2013.01);
(Continued)

(58) Field of Classification Search
CPC ...... A61B 18/1233; A61B 2018/00875; A61B 90/06; A61B 2018/00702
(Continued)

(56) References Cited

U.S. PATENT DOCUMENTS 5,366,496 A * 11/1994 Dahl et al. ..................... 607/132
5,542,916 A    8/1996 Hirsch
(Continued)

FOREIGN PATENT DOCUMENTS

CN    1211930    3/1999
CN    101084038   12/2007
(Continued)

OTHER PUBLICATIONS

Title: International Search Report and Written Opinion Citation: PCT/US2011/061475 Publication Date: Mar. 2, 2012.
(Continued)

*Primary Examiner* — Joseph Stoklosa
*Assistant Examiner* — Brian M Antiskay
(74) *Attorney, Agent, or Firm* — Dykema Gossett PLLC

(57) ABSTRACT

An electrode catheter device with indifferent electrode for direct current tissue therapies is disclosed. An example of the catheter device has a flexible tubing with at least one ablation electrode. The catheter device also may also be used with a sheath for introducing the flexible tubing inside a patient's body. An indifferent electrode on the sheath can provide a ground for a direct current (DC) pulse to deliver electrical energy and create an electrical field adjacent a tissue. Various other embodiments are also disclosed.

22 Claims, 14 Drawing Sheets

Related U.S. Application Data continuation-in-part of application No. 12/952,948, filed on Nov. 23, 2010, now abandoned.

(60) Provisional application No. 61/415,746, filed on Nov. 19, 2010.

(51) Int. Cl.
  *A61B 18/16* (2006.01)
  *A61B 5/042* (2006.01)
  *A61B 18/14* (2006.01)
  *A61B 18/00* (2006.01)
  *A61M 25/01* (2006.01)
  *A61M 25/06* (2006.01)

(52) U.S. Cl.
  CPC ............ *A61B 2018/00357* (2013.01); *A61B 2018/00613* (2013.01); *A61B 2018/00791* (2013.01); *A61B 2018/1435* (2013.01); *A61B 2018/162* (2013.01); *A61M 25/0147* (2013.01); *A61M 2025/0681* (2013.01)

(58) Field of Classification Search
  USPC ........ 600/372–374, 393, 422–424, 435, 466, 600/471; 604/95.04, 95.05; 606/27–43, 606/46–50; 607/115–124, 131
  See application file for complete search history.

(56) References Cited

U.S. PATENT DOCUMENTS

| | | | |
|---|---|---|---|
| 5,687,723 A * | 11/1997 | Avitall | 600/374 |
| 6,212,426 B1 | 4/2001 | Swanson | |
| 6,425,894 B1 * | 7/2002 | Brucker et al. | 606/41 |
| 6,974,457 B2 * | 12/2005 | Gibson | A61B 18/14 600/374 |
| 2005/0070972 A1 * | 3/2005 | Wahlstrand | A61N 1/05 607/48 |
| 2006/0041251 A1 * | 2/2006 | Odell | A61B 18/1233 606/32 |
| 2006/0167499 A1 | 7/2006 | Palti | |
| 2007/0005053 A1 * | 1/2007 | Dando | 606/41 |
| 2007/0255378 A1 * | 11/2007 | Polkinghorne et al. | 607/119 |
| 2007/0287994 A1 | 12/2007 | Patel | |
| 2008/0167643 A1 | 7/2008 | Mizrahi | |
| 2009/0099555 A1 * | 4/2009 | Viohl | A61B 1/00114 606/1 |
| 2010/0057072 A1 | 3/2010 | Roman | |
| 2010/0168827 A1 | 7/2010 | Schultz et al. | |
| 2010/0211076 A1 | 8/2010 | Germain | |

FOREIGN PATENT DOCUMENTS

| | | | |
|---|---|---|---|
| CN | 101822573 | | 9/2010 |
| JP | H09-509069 | | 9/1997 |
| JP | 2009-535182 | | 10/2009 |
| JP | 2011-508628 | | 3/2011 |
| WO | 9510318 | | 4/1995 |
| WO | 9725098 | | 7/1997 |
| WO | 01/06941 | | 2/2001 |
| WO | 2007/024983 | | 3/2007 |
| WO | 2007130900 | | 11/2007 |
| WO | WO 2010/091701 | * | 2/2009 |
| WO | 2009085458 | | 7/2009 |
| WO | 2010080974 | | 7/2010 |
| WO | 2010/091701 | | 8/2010 |

OTHER PUBLICATIONS

Supplementary European Search Report for EP Application No. 11842039, dated Mar. 10, 2015. 7 pages.

\* cited by examiner

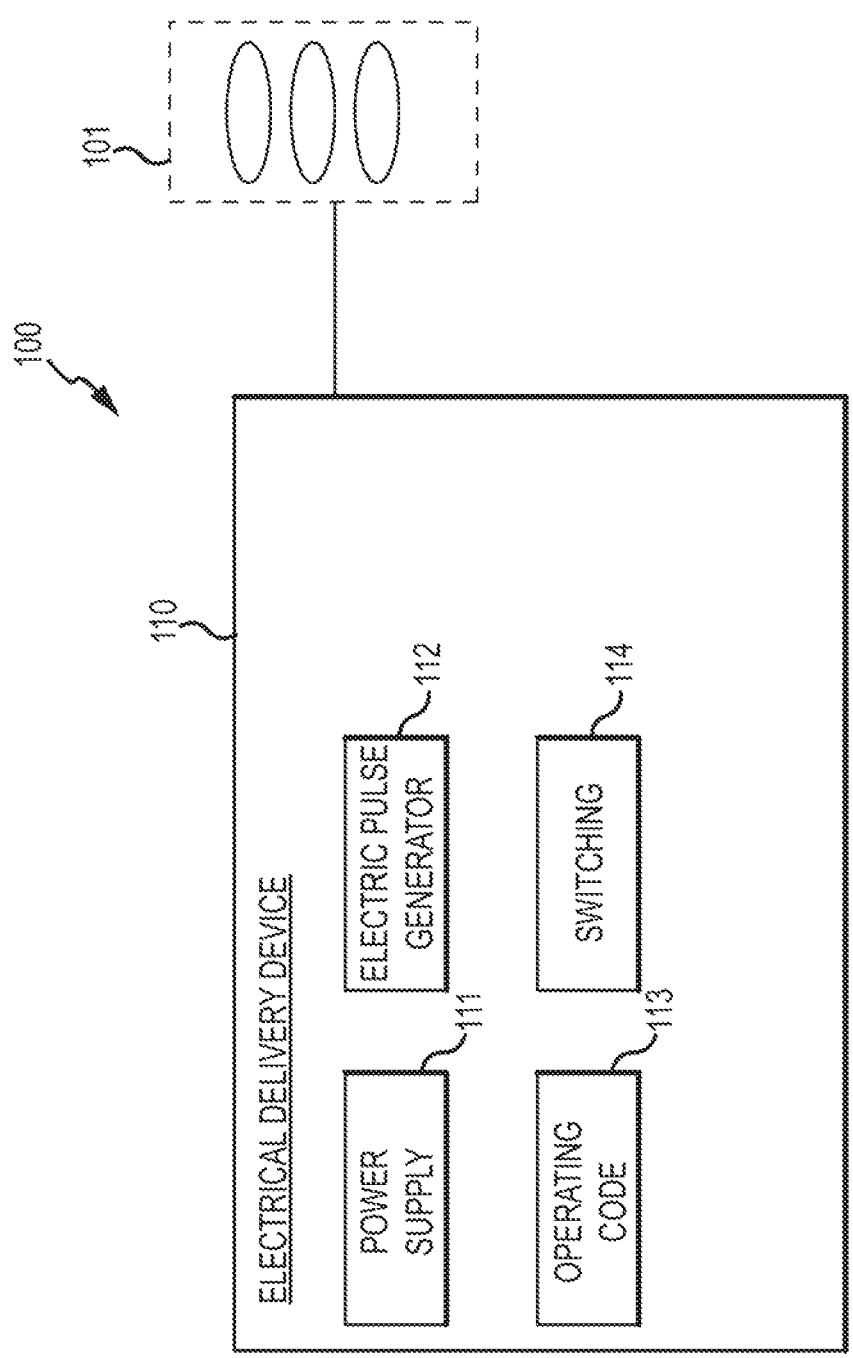

ELECTRODE CATHETER DEVICE WITH INDIFFERENT ELECTRODE FOR DIRECT CURRENT TISSUE THERAPIES

PRIORITY CLAIM

This application is a national stage filing based upon international application no. PCT/US2011/061475, filed 18 Nov. 2011 and published in English on 24 May 2012 under international publication no. WO 2012/068505, which claims priority to U.S. provisional application No. 61/415,746, filed 19 Nov. 2010 (the '746 application); U.S. non-provisional application Ser. No. 12/982,675, filed 30 Dec. 2010, now pending (the '675 application); and U.S. non-provisional application Ser. No. 12/952,948, filed 23 Nov. 2010, now abandoned (the '948 application). This application is also a continuation-in-part of the '675 application, which is a continuation-in-part of the '948 application. The '746 application, the '675 application, and the '948 application are hereby incorporated by reference as though fully set forth herein.

BACKGROUND OF THE INVENTION a. Field of the Invention

This invention relates generally to medical instruments, and more specifically, to electrode catheter devices with one or more indifferent electrodes for direct current tissue therapies.

b. Background Art

Catheters are typically flexible, tubular devices that are widely used by physicians performing medical procedures to gain access into interior regions of the body. Catheters may be used to apply energy (e.g., radiofrequency (RF) energy) to form lesions in tissue at a desired location. It is well known that benefits can be gained if the depth and location of these lesions can be controlled, which changes the electrical properties of the tissue. For example, lesions can be formed at specific locations in cardiac tissue to lessen or eliminate undesirable atrial fibrillation or other arrhythmias.

Several difficulties can be encountered, however, when attempting to form lesions at specific locations using some existing electrodes. One such difficulty encountered with existing catheters relates to how to control the energy using conventional techniques. Typically, the physician forms lesions in the tissue based on personal experience using the catheter. Such experience only comes with time, and can be quickly lost if the physician does not use the catheter on a regular basis. In addition, when forming lesions in a heart, the beating of the heart further complicates matters, making it difficult to maintain sufficient contact pressure between the catheter and the tissue for a sufficient length of time to form a desired lesion. If the contact between the catheter and the tissue cannot be properly maintained, a quality lesion is unlikely to be created. In addition, using RF may result in uneven lesion formation. For example, more RF energy may be emitted near the RF electrode and "tail-off" farther away from the RF electrode. Likewise, the RF energy emitted by adjacent electrodes may overlap, or alternatively, not fully cover the tissue area between the RF electrodes, if the electrodes are not properly spaced.

BRIEF SUMMARY OF THE INVENTION

It is desirable to be able to perform visualization (e.g., mapping) and/or tissue therapy procedures, including when in contact with a moving surface (e.g., the heart wall). The inventive techniques described, depicted, and claimed herein can be employed with conventional catheters, for example, mapping and/or lesion formation catheters. In various embodiments, catheters are disclosed that use electrical energy, e.g., a direct current (DC), to energize the electrodes and generate an electrical field for visualization techniques, and/or to form lesions of the tissue.

In an embodiment, a catheter apparatus is disclosed comprising an elongate member comprising at least one ablation electrode. A sheath is sized and configured to introduce the elongate member inside a patient's body. An indifferent electrode on the sheath is configured to allow for a current path of a direct current pulse to be delivered from the at least one ablation electrode to the indifferent electrode to create an electrical field adjacent a tissue. The current path may be formed by driving current through the indifferent electrode to the catheter ablation electrodes or by driving current through the catheter ablation electrodes to the indifferent electrode, with the indifferent electrode serving as a ground for the current path.

In an example, the DC pulse may be characterized by a variable frequency waveform. The DC pulse may also be characterized by a variable amplitude waveform. The DC pulse may also be characterized by a variable duration waveform.

In an example, the plurality of electrodes are wired together in series. In another example, the plurality of electrodes are electrically connected in series only during delivery of the DC pulse. At least one port may be formed in the flexible tubing between two or more electrodes. The port is configured to secrete a conductive fluid or gel to facilitate formation of a current path between the two or more electrodes.

In another embodiment, a steerable introducer is disclosed comprising an indifferent coil electrode configured to provide an electrical ground for a direct current pulse for lesion formation or visualization procedures.

In another embodiment, a kit is disclosed comprising a catheter comprising a proximal end, a distal end, and at least one electrode located near the distal end. The kit also includes a sheath comprising an indifferent electrode configured to allow for a current path to be formed between the at least one electrode and the indifferent electrode. For example, the indifferent electrode may be configured to provide a ground for a current path from a power source through the at least one electrode.

To improve the efficiency and efficacy of the procedure, each of the electrodes may be independently and/or selectively activated and/or energized based on electrode-tissue contact, and more specifically by electrode-tissue electrical coupling.

In at least one embodiment, the indifferent electrode may be a coil. The coil may be formed by windings. The coil may be configured to have a particular number of windings configured to provide a high surface area for dissipating heat caused by electrical energy. In addition, the coil may be configured such that a pitch of the windings (i.e., the spacing between the individual windings forming the coil) provide a high surface area for dissipating heat caused by electrical energy. The coil may also include a shunt, such as a shorting wire or wires, across some or all of the individual windings of the coil.

Still other features of electrode catheter devices with indifferent electrode for direct current tissue therapies devices are disclosed.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 10 is a high-level block diagram of an exemplary circuit which may be implemented with a tissue therapy catheter.

Corresponding reference characters indicate corresponding parts throughout the several views. The exemplifications set out herein illustrate various embodiments, in one or more forms, and such exemplifications are not to be construed as limiting the scope of the claims in any manner.

DETAILED DESCRIPTION

Figure 1:
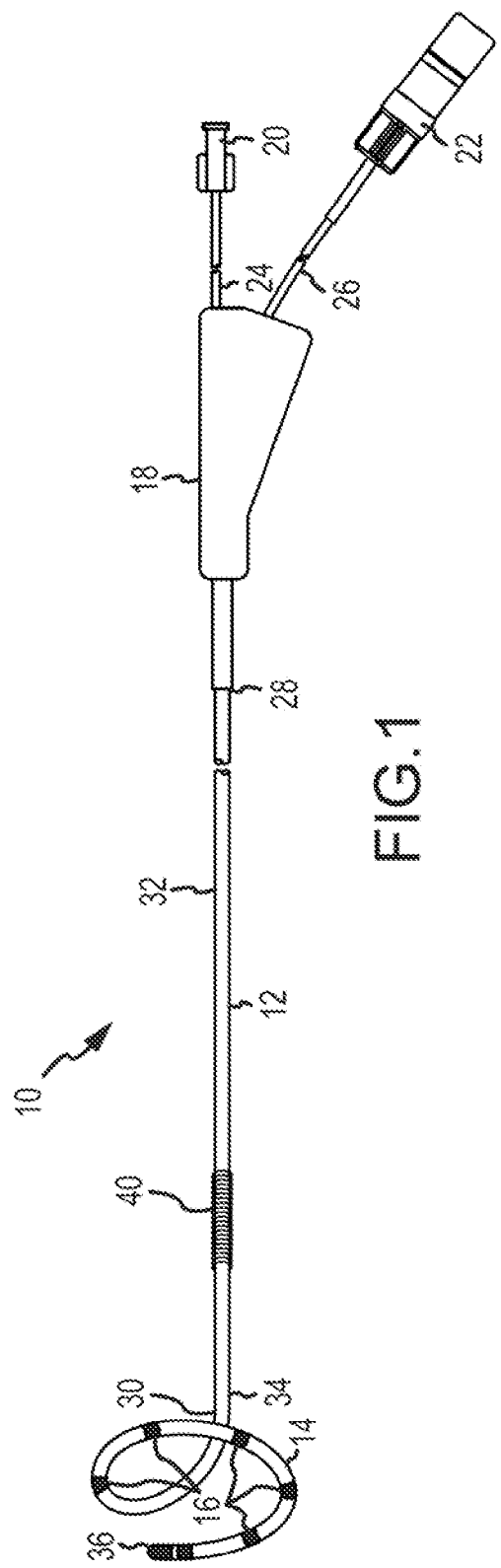
FIG. 1 illustrates an exemplary non-steerable catheter with electrodes which may be implemented for tissue therapy.

Many specific details of certain embodiments hereof are set forth in the following description in order to provide a thorough understanding of such embodiments. One skilled in the art, however, will understand that the present disclosure may have additional embodiments, or that the present disclosure may be practiced without several of the details described in the following description. All directional references (e.g., proximal, distal, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Physicians can access epicardial and/or endocardial tissue using one or more properly configured catheters to diagnose and/or therapeutically treat, e.g., ablate, tissue. Such a catheter can either be run from an inferior or superior approach into the right atrium. It can also be placed transseptally into the left atrium. Many physicians use a transseptal sheath or introducer to properly place catheters within a patient's heart and/or vasculature. In various embodiments, a catheter of the present invention may be configured with one or more direct current (DC) electrodes which generate an electrical field during operation. Further, as used herein, a "catheter" means an elongated structure that can be inserted into and/or through a body cavity, duct, and/or vessel. In at least one embodiment, a catheter may be hollow and/or define a lumen therethrough for passing another medical device, such as a guidewire or another catheter, for example. However, in various embodiments, a catheter may be closed at least at its distal end.

The electrodes may be implemented for cardiac mapping and/or delivery of tissue therapy during one or more cardiac procedures. In at least one embodiment, a catheter in a hoop configuration (e.g., a lasso-like configuration) can provide a consistent, circumferential lesion around the pulmonary veins, either with a single pulse or with multiple pulses, by positioning the electrodes in a ring.

Other types and configurations of electrodes can also be used. For example, a number of smaller rigid electrodes can be used instead of a larger electrode so that the tip assembly is more flexible. In another example, a segmented electrode can be used. A suitable segmented electrode structure is disclosed in U.S. Pat. No. 6,171,306, entitled "Systems and Methods for Forming Large Lesions, in Body Tissue Using. Curvilinear Electrode Elements," which is hereby incorporated by reference as though fully set forth herein.

In an exemplary embodiment, a segmented electrode may be about 1.3 mm in diameter, but could be made as small as 1.0 mm in diameter and as large as 3.3 mm in diameter. In this arrangement, the electrode is about 5 cm in total length.

In an alternative embodiment of a segmented electrode, there can be two or more spaced apart electrodes. In this arrangement, power is delivered in parallel to each segmented electrode. This decreases the effect of voltage gradients within each segmented electrode, which, in turn, improves the uniformity of current density delivered by the electrode. The spacing between the multiple wires serving each electrode segment can be selected to achieve the desired uniformity of current density.

The electrode may also be configured to reduce or eliminate the so-called "edge effects" between adjacent therapy delivery electrodes. Edge effects may result in inconsistent lesion depths. In addition, lesions formed using electrical pulses have different characteristics than those obtained with RF. That is, the lesions formed by the electrical field from the tissue therapy catheter may not form fibrotic tissue, and may eventually heal to be vital myocardium, while still maintaining electrical isolation.

The embodiments described herein may include both a physical device (the catheter) and software or other control means which may control energy delivery and electric field formation, as well as sensory functions. In use, the catheter may be operated using lower currents delivered to the electrodes for mapping or pacing procedures. Higher currents may be delivered to the electrodes to cause electroporation-like effects and/or lesion formation upon a portion of target tissue.

Electroporation involves changes in a cell membrane's permeability due to a voltage gradient applied across and/or through the membrane. The charge of the lipid molecules found in the cellular membrane redistribute in the presence of an atypical voltage gradient, thereby creating or enlarging hydrophilic pores. Cells also naturally allow some small ions through their lipid bilayer. These ions are also affected by the voltage gradient creating current. The current generates Joule heating which has a thermal phase inducing effect on the lipid bilayer. These reactions create larger than normal pores in the cell membrane.

"Reversible" electroporation (RE) occurs when the pores are able to reseal themselves. Reversible electroporation may be used for drug delivery procedures. That is, the pores may be opened, and a fluid containing the drug may be delivered adjacent the pores. After delivery of the fluid, and having provided sufficient time for the drug to enter through the cell wall, the electric current is discontinued and the pores allowed to reseal.

"Irreversible" electroporation (IRE) occurs if a cell is exposed to a voltage gradient for more than a threshold time, and/or if the voltage gradient exceeds the dielectric strength of the cell. In IRE, the cell is unable to reseal the pores, and the cell dies. Accordingly, IRE may be used in lesion formation procedures to alter the electrical pathways that initiate and/or maintain atrial fibrillation.

Herein notions relating to both reversible and irreversible electroporation may be used with controlled delivery of bursts or pulses of electricity to create an electric field and generate the desired voltage gradient in the tissue during a procedure. For example, a series of electrical pulses may be used having a pulse width on a micro- or even nano-second scale. Variations in pulse amplitude, frequency, and/or duration may also be used to control a given electrical pulse delivered to the electrodes. This controlled delivery may reduce or altogether eliminate thermal damage to surrounding tissue, and thus can be used for highly targeted cardiac tissue therapies and/or mapping procedures with good results.

Exemplary embodiments may employ any of a wide variety of different types and configurations of catheters with DC-based electrodes. See, e.g., FIGS. 1, 3, and 4A-C. In one example, a catheter may be implemented with an introducer or sheath (see, e.g., FIGS. 2 and 3) which may be positioned at the target location inside the patient's body and then used with a mapping system for positioning of a catheter and carrying out the medical procedure. In other examples, the DC-based electrodes may be placed on the catheter itself for mapping and/or lesion formation procedures.

As will become apparent from the following description, the electrical bursts or pulses may be implemented with a single catheter, or with multiple (e.g., two or more) catheters that are utilized in conjunction with one another to create an electric field that may be used for mapping, therapy, and/or other medical procedures. The catheter may be a standard linear catheter. In still other examples, the catheter may be implemented as a shaped (e.g., curvilinear) catheter including one or more electrodes (e.g., for lesion formation, other therapy, and/or mapping procedures), and in addition, may include temperature sensors (or other sensors and feedback mechanisms), and/or irrigation ports. These and other modifications will be readily understood by one having, ordinary skill in the art after becoming familiar with the teachings herein.

Figure 3:
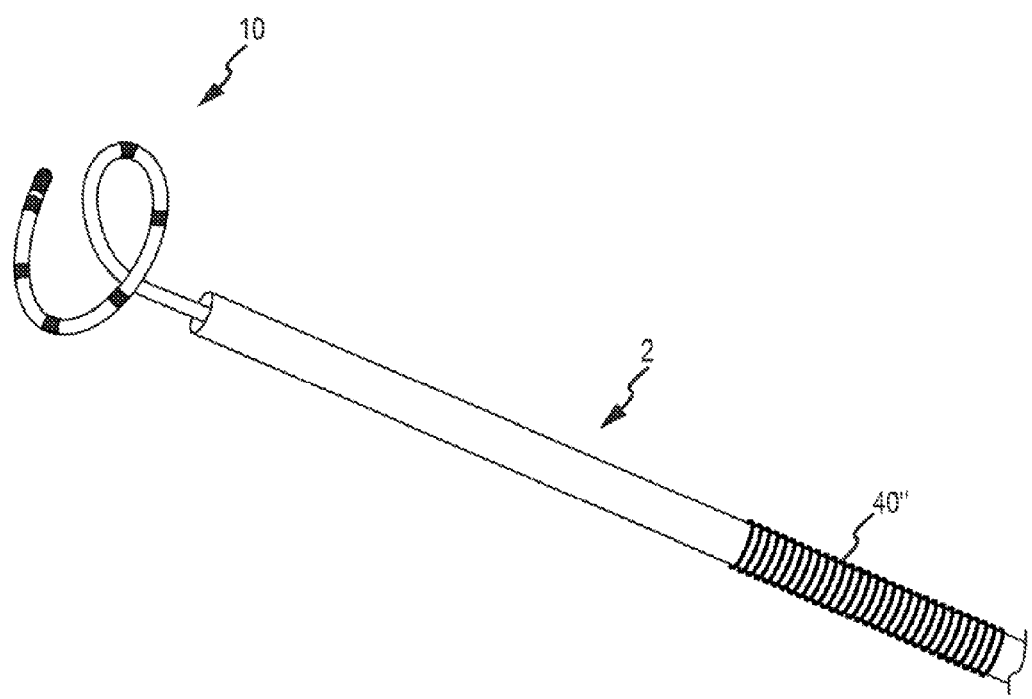
FIG. 3 shows an exemplary tissue therapy catheter as it may be inserted through a sheath such as a guiding introducer.

By way of a specific example, FIG. 1 illustrates an exemplary single-use catheter 10. For purposes of illustration, but not intending to be limiting, the catheter 10 generally includes a flexible outer tube (or tubing) 12, a tip assembly 14, at least one electrode 16, a Y connector 18, a luer device 20, and an electrical connector 22. The catheter 10 is shown in FIGS. 1 and 3 as it may be implemented as a non-steerable catheter 10. However, in at least one embodiment a tissue therapy catheter may be steerable.

In various embodiments, an electrical current path may be formed between a power source (not shown), one or more of the electrodes 16, and a ground. By way of example, a coaxial cable or other conductor having a known and/or controllable impedance may be used as an electrical conductor to deliver an electrical pulse to the electrodes. Such an embodiment may be particularly advantageous in the case of ultra-short duration pulses, because other wiring may not preserve the sharp edges on the pulse boundary. The electrodes 16 can be seen in more detail, for example, in FIG. 5, and discussed in more detail below. Although a skin patch may be implemented as the ground, this generally causes undesirable body movement due to the high impedance of the system. That is, energy must travel from the tissue near the electrodes, and through the patient's body to get to the skin patch.

Previously, direct current application of electrical energy to a patient's body may have resulted in undesirable results. During such procedures, skeletal muscle contraction and nerve stimulation may result in violent movements and considerable transient and persistent pain. Bone fracture and tendon rupture have occasionally been reported. Accordingly, in one embodiment, RF-type (or other frequency-based) signals oscillate sufficiently rapidly to avoid muscle stimulation and therefore avoid causing cardiac muscle depolarization. However, from the external and the implantable (device) side of implantable cardioverter-defibrillator (ICD) usage, years of experience with various truncated waveforms are well known (e.g., where shocks of 2-20 ms duration are themselves made from 10-1000 ρs pulses) for lower defibrillation thresholds, reduced pain, and less muscular movement has not yet been found to substantially improve these problems.

Accordingly and with reference to FIG. 1, instead of or in addition to a skin patch, the catheter 10 may be provided with an indifferent electrode 40 configured to serve as the ground in at least one embodiment. For example, the indifferent electrode 40 may be implemented as a conductive coil, comprising a metal such as platinum, for example, on the exterior of the catheter 10. Positioning a ground in the form of indifferent electrode 40 on the catheter 10 such that the electrode 40 may be located inside of the patient's body may significantly decrease movement of the patient during delivery of the DC current (e.g., via electrical bursts or pulses). One embodiment of an indifferent electrode 40 can be seen in more detail in FIG. 6.

Although it will become evident that aspects of exemplary catheter 10 are applicable to a variety of medical procedures and end uses, the embodiments will be described principally in the context of a specific example of the catheter 10 shown in FIG. 1. Specifically, catheter 10 is believed to be particularly advantageous as a therapy delivery catheter for creating endocardial lesions during cardiac procedures to treat arrhythmias, and also for cardiac electrophysiological mapping and delivering diagnostic pacing stimuli. However, the description and the appended claims are not intended to be limited to any specific example, including but not limited to specific examples or embodiments described herein, except when explicitly defined as such in the appended claims. That is, a hybrid combination of endocardial- and epicardial-access can also be used for tissue therapy procedures.

Again with reference to FIG. 1, a Y-connector 18 separates an inner tube 24 from electrical lead wires 26 extending between electrical connector 22 and both tip assembly 14 and indifferent electrode 40. More specifically, tube 24 and the lead wires 26 forward of Y-connector 18 pass internally through outer tube 12, while aft of Y-connector 18, inner tube 24 and leads for the lead wires 26 are exposed and separated for connection to a fluid source (not shown) and a power source (not shown), respectively. In one embodiment, electrical connector 22 is a known connector configured to engage the power source or a power supply with for example, a plug-in connection. One suitable electrical connector may be a 14-pin REDEL® plastic connector commercially available from LEMO of Rohnert Park, Calif., although other connectors from various manufacturers may likewise be utilized.

Outer tube 12 includes a proximal end 28 coupled to Y-connector 18, a distal end 30 coupled to tip assembly 14, and an axial length extending between proximal end 28 and distal end 30. In general, it will be appreciated that the terms "proximal" and "distal" may be used in this and other embodiments with reference to a clinician manipulating one end of an instrument, such as catheter 10, used to treat a patient. Typically, the term "proximal" refers to the portion of the instrument closest to the clinician and the term "distal" refers to the portion located furthest from the clinician. In one embodiment, flexible tubing 12 may be fabricated according to known processes, such as multilayer processing including extrusion processes, mandrel-based processes and combinations thereof from any suitable tubing material known in the art of medical instruments, such as engineered nylon resins and plastics, including but not limited to PEBAX® tubing of Ato Fina Chemicals, France.

Although not required, in an exemplary embodiment, tubing 12 may be fabricated from a first tubing material, defining a first portion 32 of tubing 12 more proximal to the Y-connector 18, and the tubing 12 may be fabricated from a second tubing material defining a second portion 34 of tubing 12 more proximal the tip assembly 14. Additional tubing material may be used to define other portions of tubing 12, and even the tip assembly 14. By fabricating first portion 32, second portion 34, and/or other portions from different materials and/or grades of materials, tubing 12 may have varying flexible properties, and is sometimes referred to as a multi-flexible tube.

For example, in one embodiment, the first material defining first portion 32 of tubing 12 may be a comparatively rigid and kink resistant braided material. First portion 32 may be formed with different portions of braided material, semi-soft material, and soft material fused to one another so that first portion 32 becomes increasingly flexible along the axial length as first portion 32 approaches tip assembly 14. The second material defining second portion 34 of tubing 12 may be a softer material having flexible properties. In the illustrated embodiment, each of the tubing portions 32, 34 share a common outside diameter of, for example, 7 French, although in other embodiments, tubing portions 32, 34 may have varied diameters.

As shown in FIG. 1, first portion 32 extends for a majority of the axial length of tubing 12 between proximal end portion 28 and distal end portion 30. Second portion 34 of tubing 12 extends for a shorter length than the length of first portion 32. By way of example only, in a specific embodiment first portion 32 extends for an axial length of about 126.3 cm, and second portion 34 extends for an axial length of about 2.2 cm, although other relative lengths of the tube portions may likewise be employed in other embodiments. The different relative lengths of tube portions 32, 34, as well as the different flexible properties of tube portions 32, 34, allow tip assembly 14 to be more precisely positioned within a patient's body, while also avoiding problems of kinks and excessive deflection of tubing 12 along the majority of its length during use and handling.

Figure 2:
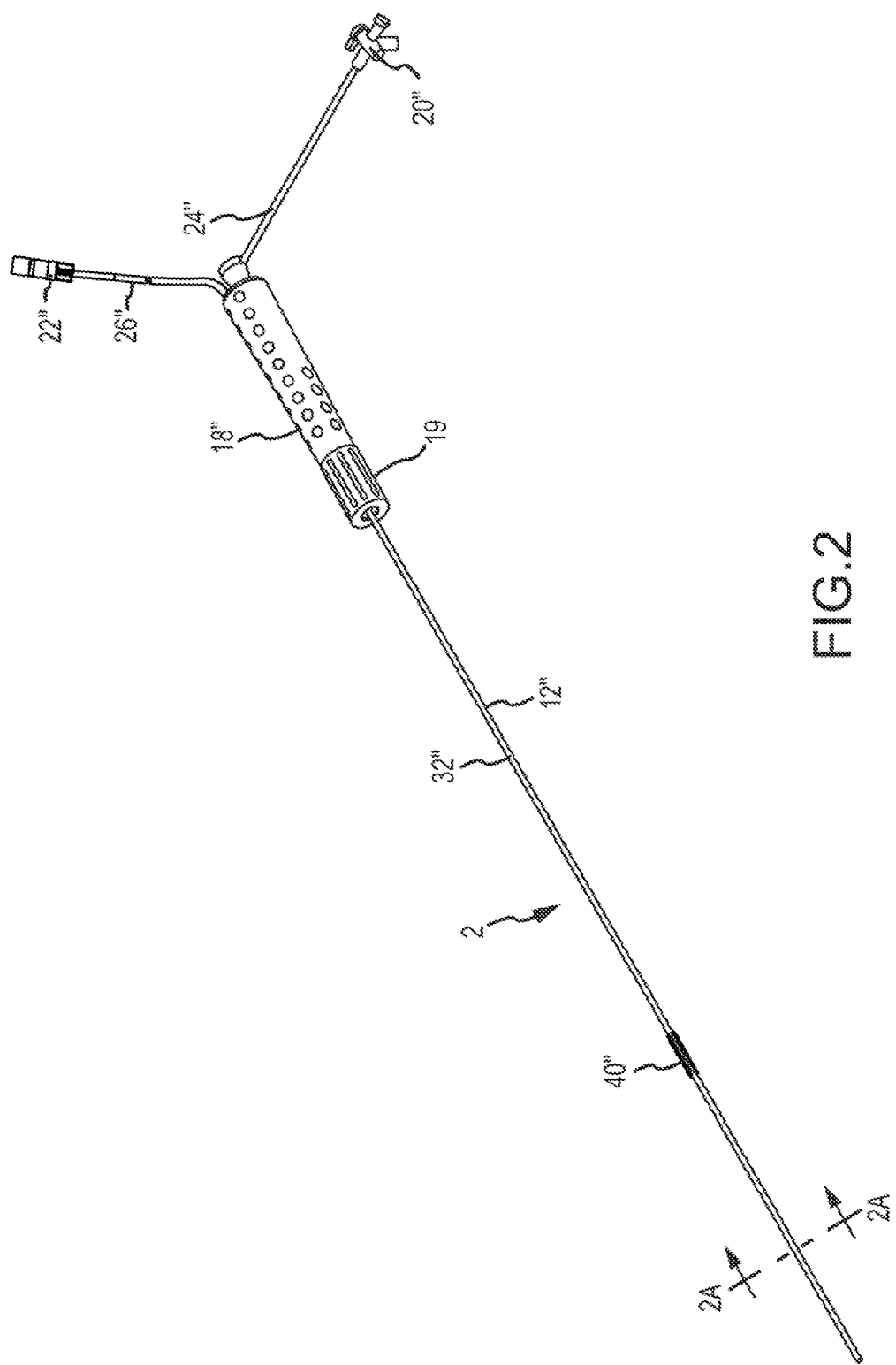
FIG. 2 illustrates an exemplary steerable catheter sheath with at least one electrode which may be implemented for tissue therapy.
Figure 2A:
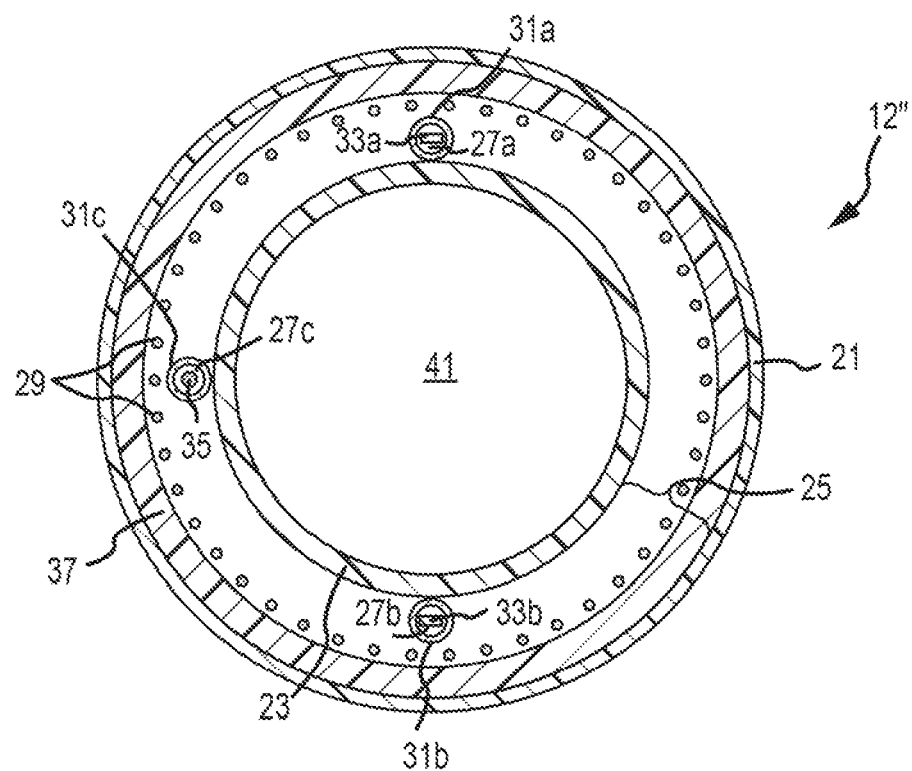
FIG. 2A is a cross-sectional view of the sheath of FIG. 2, taken along lines 2A-2A in FIG. 2.

In at least one embodiment, a catheter may also be implemented with a steerable introducer or sheath 2, an exemplary embodiment of which is shown in FIG. 2. Like components are referred to with the double-prime (") designation, for example, indifferent electrode 40". A handle 18" may be provided at a proximal end of the shaft 12". The handle 18" and shaft 12" may carry a steering mechanism for selectively bending or flexing the shaft 12" in at least two opposite directions. An electrode, such as indifferent electrode 40" may be positioned on or within shaft 12" at a position at or proximal to a distal end of the shaft 12". FIG. 2A shows a cross-sectional view of an exemplary embodiment of the shaft 12", at a final stage of assembly following the performance of a reflow process on at least a portion of the shaft 12".

Referring to FIG. 2A, in this embodiment, and in its most general form, the shaft 12" comprises an inner liner 23 and an outer layer 25. In at least one embodiment, a heat shrink tube 21 may further surround the outer layer 25. The inner liner 23 has an inner surface and an outer surface, where the inner surface defines a major lumen 41. In an exemplary embodiment, the inner liner 23 may be formed of extruded polytretrafluoroethylene (PTFE) tubing, such as, for example, Teflon® tubing. In one exemplary embodiment, the PTFE comprises etched PTFE. An inner liner formed of this particular material creates a lubricious lumen within which other medical devices used with the sheath, such as, for example, catheters, needles, dilators, and the like, can be passed. The inner liner 23 may be relatively thin. For example, in one embodiment, the inner liner 23 has a thickness on the order 0.0015 inches (0.0381 mm). It will be appreciated by those having ordinary skill in the art that the inner liner 23 can be formed of a material other than PTFE, or etched PTFE. For example, in other exemplary embodiments, the inner layer 23 may be comprised of polymeric materials, such as, for example and without limitation, polyether block amides, nylon, and other thermoplastic elastomers. Accordingly, sheaths having inner liners made of materials other than PTFE remain within the spirit and scope of the present disclosure.

With continued reference to FIG. 2A, the outer layer 25 may be disposed adjacent to the inner layer 23, and the outer surface thereof. In an exemplary embodiment, the outer layer 25 includes one or more minor lumens 27a-c therein and coupled thereto adapted to receive and house deflectable elements, such as, for example, steering or pull wires associated with a steering mechanism for the sheath, or elongate conductors (e.g., electrical wires) coupled to the indifferent electrode 40". Because the major lumen 41 of the shaft 12" may ideally be kept open to allow for the uninhibited passage of other medical devices therethrough, the minor lumens 27a-c are disposed within the outer layer 25 of the shaft 12".

The outer layer 25 can be formed of a single polymeric material, or alternatively, a combination of different components/materials (e.g., various tubing and braid assemblies) that, after the application of a reflow process on at least a portion of the shaft 12", combine to form the outer layer 25. In the exemplary embodiment illustrated in FIG. 2A, the outer layer 25 comprises one or more layers of polymeric material that are placed over the inner liner 23. The polymeric material can be in the form of one or more extruded polymer tube(s) 37 sized so as to fit over the inner layer 23. The polymer tube 37 can comprise one or more of any number of polymeric materials, such as, for example and without limitation, polyether block amides (e.g., Pebax®), polyamides (e.g., nylon), PTFE, etched PTFE, and other thermoplastic elastomers.

The polymer tube 37 can be formed of a single piece of tubing or multiple pieces of tubing. Whether formed of a single piece or multiple pieces, the tube 37 can have a uniform hardness or durometer throughout. Alternatively, different portions of the tube 37 can have different durometers (e.g., the shaft 12" can have a variable durometer from the proximal end to the distal end). In an embodiment where the tube 37 may be formed of multiple pieces, the pieces can be affixed together end to end, or portions of adjacent pieces can overlap each other. These pieces can be coupled or bonded together to form the shaft 12" during a reflow process performed thereon. Additionally, in an exemplary embodiment, one or more portions of the tube 37 disposed at the distal end of the shaft 12", or at any other location on the shaft 12" at or near where electrode 40" may be mounted, are formed so as to be translucent or transparent. The use of transparent or translucent material allows one to locate and access the minor lumen(s) 27a-c in the outer layer 25.

In an exemplary embodiment, and as illustrated in FIG. 2A, the outer layer 25 further comprises a braided wire assembly 29 disposed adjacent to and between both the inner liner 23 and the polymeric material or tube 37. The arrangement and configuration of the braided wire assembly 29 and the tube 37 may be such that the polymeric material of the tube 37 melts and flows into the braid of the braided wire assembly 29 during a reflow process performed on the shaft 12". The braided wire assembly 29, which can extend the entire length of the shaft 12" (i.e., from the proximal end to the distal end) or less than the entire length of the shaft 12", may help maintain the structural integrity of the shaft 12", and also provide an internal member to transfer torque from the proximal end to the distal end of the shaft 12".

In an exemplary embodiment, the braided wire assembly 29 comprises a stainless steel braid where each wire of the braid has a rectangular cross-section with the dimensions of 0.002 inches×0.006 inches (0.051 mm×0.152 mm). It will be appreciated by those having ordinary skill in the art, however, that the braided wire assembly 29 can be formed of material other than, or in addition to, stainless steel. For example, in another exemplary embodiment, the braided wire assembly 29 comprises a nickel titanium (also known as nitinol) braid. Additionally, the braided wire assembly 29 can have dimensions or wire sizes and cross-sectional shapes other than those specifically provided above, such as, for example, a round or circular cross-sectional shape, and also include varying braid densities throughout. Different braid wire sizes allow different shaft torque and mechanical characteristics. Accordingly, braided wire assemblies comprising materials other than stainless steel, and/or dimensions other than those set forth above, remain within the spirit and scope of the present disclosure.

As briefly described above, in an exemplary embodiment, the outer layer 25 further includes one or more minor lumens 27a-c disposed therein and coupled thereto. Each minor lumen 27a-c may be adapted to receive and house either an electrical wire or wires associated with electrode 40", or a deflectable element, such as a pull wire, of the steering mechanism of the sheath. In an exemplary embodiment, the sheath includes one or more extruded tubes 31 (i.e., tubes 31a-b housing pull wires 33a-b, and tube 31c housing electrode wiring 35 seen in FIG. 2A). Each of the tubes 31a-c define a corresponding minor lumen 27a-c. The tubes 31a-c, which are also known as spaghetti tubes, can be formed of a number of materials known in the art, such as, for example and without limitation, PTFE. In an exemplary embodiment, the tubes 31a-c are formed a material having a melting point higher than that of the material in polymer tube 37 so that the tubes 31a-c will not melt when the shaft 12" is subjected to a reflow process. In the embodiment illustrated in FIG. 2A, the tubes 31a-c are affixed or bonded to the outer surface of the inner layer. The tubes 31a-c can be affixed in a number of ways, such as, for example, using an adhesive. One suitable adhesive may be cyanoacrylate. Once the shaft 12" is subjected to a reflow process, the polymeric material of the tube 37 surrounds and encapsulates the tubes 31a-c resulting in the tubes 31a-c, and therefore the minor lumens 27a-c, being disposed within the outer layer 25.

The minor lumens 27a-c extend axially relative to the longitudinal axis of the shaft 12". In an exemplary embodiment, some or all of the minor lumens 27a-c that house electrical wire 35 associated with the indifferent electrode 40" extend from a proximal portion of the shaft 12" to a distal portion of the shaft". In another exemplary embodiment, some or all of the minor lumens 27a-c extend from the proximal end of the shaft 12" to various points or locations on the shaft 12" between the proximal and distal ends. For example, the minor lumen 27c that houses the electrical wire 35 of the indifferent electrode 40" can extend from the proximal end of the shaft 12" to a distal portion of the shaft 12". Alternatively, it can extend from the proximal end to the point on the shaft 12" at or near where the indifferent electrode 40" may be mounted. Similarly, minor lumens 27a-b that house the pull wires 33a-b of the steering mechanism (i.e., the lumens 31a and 31b in FIG. 2A) can extend from the proximal end of the shaft 12" to a pull ring (not shown) positioned at or near the distal end of the shaft 12". Alternatively, they can extend from the proximal end to a point in the shaft 12" that the pull wires 33a-b are coupled to another component of the steering mechanism, such as a pull ring (not illustrated). Further, in at least one embodiment, a second electrical wire (not shown) may be at least partially positioned in another minor lumen (not shown) that extends to the indifferent electrode. In any event, the electrical wire 35 may be connected to a portion of the indifferent electrode 40", such as a proximal end of the electrode 40" and/or the second wire may be connected to another portion of the indifferent electrode 40", such, as a distal end of the electrode 40". The electrical wire 35 or wires may thereafter pass through shaft 12", handle 18", and external wiring 26" to an electrical connector 22", which may be configured to be connected to a power source and/or grounded.

In an exemplary embodiment, the shaft 12" may be steerable (i.e., the distal end of the shaft 12" can be deflected in one or more directions relative to the longitudinal axis). In one exemplary embodiment, the movement of the shaft 12" can be controlled and operated manually by a physician. In another exemplary embodiment, however, movement can be controlled and operated by an automated guidance system, such as, for example and without limitation, a robotic-based system and/or a magnetic-based system.

In an exemplary embodiment where the sheath 2 may be configured for physician control, the sheath 2 includes a steering mechanism. A detailed description of an exemplary steering mechanism is set forth in U.S. Patent Publication No. 2007/0299424 entitled "Steerable Catheter Using Flat Pull Wires and Method of Making Same" filed on Dec. 29, 2006, the disclosure of which is hereby incorporated by reference in its entirety. Accordingly, the steering mechanism is only briefly described herein. In an exemplary embodiment, the steering mechanism comprises a handle, a pull ring disposed in the shaft 12", and one or more deflection elements, such as pull wires, coupled with both the handle and the pull ring, and disposed within the shaft 12".

As illustrated in FIG. 2, the handle 18" may be coupled to the shaft 12" at the proximal end thereof. In an exemplary embodiment, the handle 18" provides a location for the physician/clinician to hold the shaft 12" and, in an exemplary embodiment, is operative to, among other things, effect movement (i.e., deflection) of the distal end of the shaft 12" in one or more directions. The handle 18" is conventional in the art and it will be understood that the construction of the handle 18" can vary.

In an exemplary embodiment, the handle 18" includes an actuator 19 disposed thereon or in close proximity thereto, that may be coupled to the pull wires of the steering mechanism. The actuator 19 may be configured to be selectively manipulated to cause the distal end to deflect in one or more directions. More particularly, the manipulation of the actuator 19 causes the pull wires to be pushed or pulled, thereby effecting movement of a pull ring (not shown) disposed in a distal portion of the shaft 12", and thus, the shaft 12". The actuator 19 can take a number of forms known in the art. For example, the actuator 19 can comprise a rotatable actuator 19, as illustrated in FIG. 2, that causes the shaft 12" to be deflected in one direction when rotated one way, and to deflect in another direction when rotated in the other way. Additionally, the actuator 19 can control the extent to which the shaft 12" is able to deflect. For instance, the actuator 19 can allow the shaft 12" to deflect to create a soft curve of the shaft. Additionally, or in the alternative, the actuator 19 can allow the shaft 12" to deflect to create a more tight curve (e.g., the distal end of the shaft 12" deflects 180 degrees relative to the shaft axis). It will be appreciated that while a rotatable actuator 19 is described in detail here, the actuator 19 can take on any form known in the art that effects movement of the distal portion of a sheath or other medical device.

The actuator 19 may be coupled to the pull wires of the steering mechanism. In an exemplary embodiment, and as with the electrical wire associated with the indifferent electrode 40", the pull wires 33a-b are located within the outer layer 25 of the shaft 12". More particularly, the pull wires 33a-b are disposed within minor lumens 27a and 27b in the outer layer 25, and are configured to extend from the handle 18" to the pull ring. In an exemplary embodiment, the pull wires 33a-b have a rectangular cross-section. In other exemplary embodiments, however, the pull wires 33a-b can have a cross-sectional shape other than rectangular, such as, for example and without limitation, a round or circular cross-sectional shape.

The steering mechanism can comprise a number of different pull wire arrangements. For instance, in the exemplary embodiment illustrated in FIG. 2A, the steering mechanism includes two pull wires. In this particular embodiment, the pull wires are disposed 180 degrees apart from each other. In another exemplary embodiment, the steering mechanism comprises four pull wires. In such an embodiment, the pull wires are spaced 90 degrees apart from each other. Additional details of such steerable sheaths may be found in U.S. patent application Ser. No. 13/162,392, entitled "Medical Devices Having Flexible Electrodes Mounted Thereon," which is hereby incorporated by reference as though fully set forth herein.

In various embodiments, the steering mechanism may vary. For example, the steering mechanism may include a rotating cam wheel with an external steering lever. The cam wheel may hold the proximal ends of right and left steering wires. Additional details of at least one such embodiment of a steering mechanism is disclosed in U.S. Pat. No. 8,000,764, entitled "Electrophysiology/Ablation Catheter Having Second Passage," which is hereby incorporated by reference as though fully set forth herein. Further, at least another embodiment of a steering mechanism is disclosed in U.S. Pat. No. 7,881,809, entitled "Electrophysiology/Ablation Catheter and Remote Actuator Therefor," which is hereby incorporated by reference as though fully set forth herein.

FIG. 3 shows an example of tissue therapy catheter 10 as it may be inserted through a sheath 2 such as a guiding introducer. In at least one embodiment, the catheter 10 seen in FIG. 1 may be inserted through the sheath 2 shown in FIG. 2. This can allow for the indifferent electrode 40" to be positioned separately from the tip electrode 36 and/or the electrodes 16 on the catheter 10. Accordingly the catheter 10 can be placed at a desired location in the body, for example, a location in the heart where it may be desired to deliver tissue therapy, while the indifferent electrode 40" on the sheath 2 may be positioned separately at a location that may be advantageous for the desired procedure, e.g., at a location that will minimize the side effects of therapy delivery on the patient. Additionally, when catheter 10 is used with an introducer, such as sheath 2, the indifferent electrode 40 (FIG. 1) of the catheter 10 may be at least partially covered by the sheath 2 as seen in FIG. 3. Accordingly, by including the indifferent electrode 40" on the sheath 2, the indifferent electrode 40" may be more readily available to serve as a ground for current flowing from the electrode(s) 16, 36 than would indifferent electrode 40 on the catheter 10.

Figure 4A:
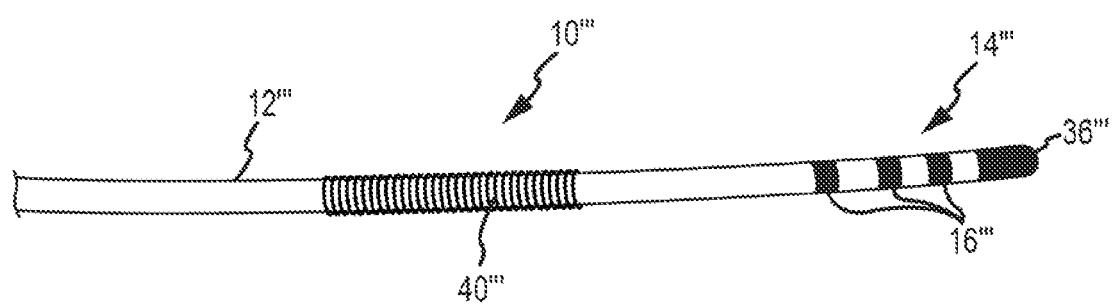
FIG. 4A shows another embodiment of a tissue therapy catheter where the tip assembly of the catheter has a substantially straight configuration.
Figure 4B:
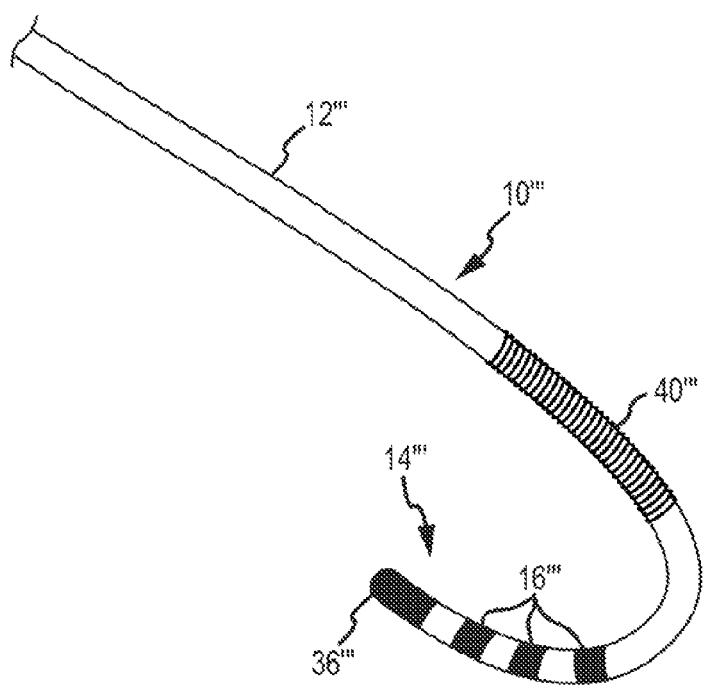
FIG. 4B illustrates the tip assembly of the catheter shown in FIG. 4A in a U-shaped configuration.
Figure 4C:
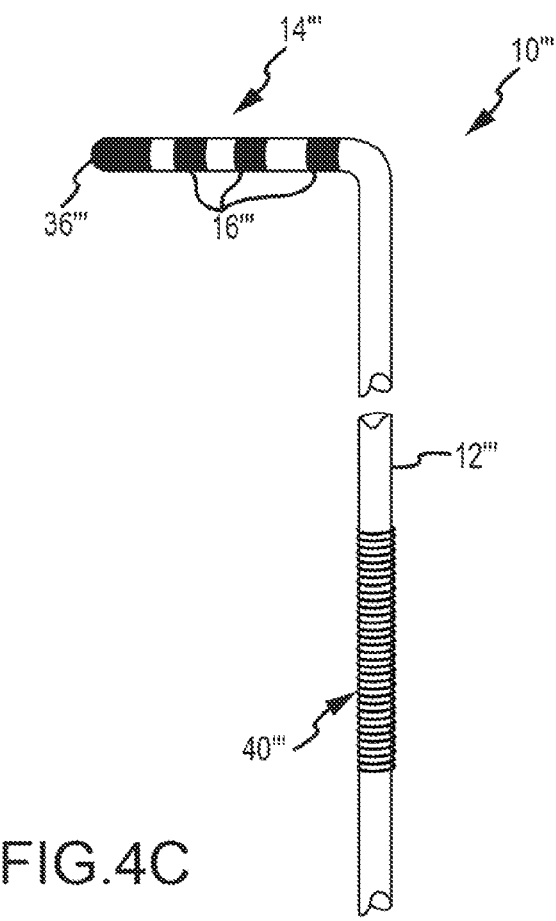
FIG. 4C illustrates the tip assembly of the catheter shown in FIG. 4A in an L-shaped configuration.

As noted above, a catheter, according to at least one embodiment, may be steerable. Operational examples of a steerable catheter 10''' are shown in FIGS. 4A-C. Like components are referred to with the triple-prime ('''') designation, for example, indifferent electrode 40'''. FIG. 4A shows the tissue therapy catheter 10''' where the tip assembly 14''' of the catheter may be in a substantially straight configuration. FIG. 4B illustrates the tip assembly 14''' of the catheter 10''' shown in FIG. 4A moved to a substantially U-shaped configuration. FIG. 4C illustrates the tip assembly 14''' of the catheter 10''' shown in FIG. 4A moved to a substantially L-shaped configuration.

With reference again to either the steerable or non-steerable embodiments of the catheter it is noted that an electrical connector 22 (see FIG. 1) may be provided to establish an electrical connection with a power source (not shown) that operates electrodes 16 of tip assembly 14 to perform, for example, tissue therapy procedures, mapping or pacing procedures, or to perform other aspects of a medical procedure.

In an exemplary embodiment the outer surface of the shaft, in particular, the sheath may have minor lumens disposed therein for the electrical wires associated with the electrodes 16. A flexible circuit (not shown) comprising one or more electrical conductors may be disposed within the outer surface of the sheath. The flexible circuit can extend from the proximal end of the shaft to the distal end. Alternatively, the flexible circuit can extend from the proximal end to a point on the shaft at which the electrode(s) are mounted. The flexible circuit may be configured for electrical coupling with one or more of the electrodes 16. Accordingly, the number of electrical conductors in the flexible circuit will at least equal the number of electrodes 16.

In various embodiments, a tissue therapy catheter may be manufactured with two PTFE wire lumens that are glued to the main sheath lumen during the manufacturing process. Next, a braid may be stretched over the assembly, and Pebax and Nylon may be reflowed over the braid.

To manufacture a tissue therapy catheter or sheath with a coil (e.g., the reference or indifferent electrode 40 shown in FIG. 1, or the indifferent electrode 40" shown in FIG. 2, or the related embodiments), at least two more PTFE lumens may be attached to accommodate the coil wires or "windings." A thinner-walled plastic (either Pebax or Nylon) may be used underneath the coil to limit the increase in outside diameter caused by the coil. In one example, the coil may be made of a 0.007" diameter Platinum wire (e.g., about a 90% Platinum and 10% Iridium alloy). The wire may be coiled around the catheter or sheath shaft using a coiling machine. Then, both ends of the coil are bonded in place by, for example, a gluing and/or reflow process The coil wires may be spaced apart and/or in electrical connection with one another. The specific configuration will depend on various design considerations, which are within the scope of knowledge of one having ordinary skill in the electrical arts after becoming familiar with the teachings herein as those teachings are applied in the medical field. In an exemplary embodiment where the windings of the coil may be electrically coupled together, thereby causing electrical energy to be shorted or shunted across the coil. This decreases the effect of voltage gradients within each segment of the coil, which, in turn, improves the uniformity of current density delivered by the electrode(s). The spacing between the multiple windings of the coil can be selected to achieve the desired uniformity of current density. Additionally, in such embodiments, the heating of the coil may also be reduced or minimized by reducing the length of coil through which current must pass.

Electrode wires may be strung down each of the wire lumens and the ends soldered to the coil's platinum wire coil ends. Next, the solder joints may be pulled inside the wire lumens of the shaft. A UV-cured adhesive may be used to cover the hole in which each wire enters a lumen. The result may be a very smooth transition around the coil of the indifferent electrode 40 as it enters the shaft 12 of the catheter 10.

A transparent polymer may be used underneath the coil of the indifferent electrode 40. This allows the manufacturer to see the wire lumens to punch or otherwise form a hole that the wire enters through. It may be also possible to use two small transparent sections underneath the two places where the holes will be punched. The entire length of the catheter may be made of transparent polymer for case of assembly.

One embodiment may use a braid having variable picks per inch. A very low picks per inch section of braid may be positioned underneath the coil. This allows for a wide clearance between braid wires for the electrical wires to pass. Because the coil may be used for electrical bursts or pulses (high voltage and current), electrical shorting to the braid may be a concern. The wide picks increase and/or maximize the amount of plastic between electrical wire and braid wire. In another embodiment, the braid picks may be manually spread at the points where the wire enters to accomplish the same result. Alternatively, the catheter 10 may be made without braid to decrease and/or prevent energy loss within the catheter, as well as to maximize safety.

Referring to FIG. 1, in operation, a distal end portion 30 of catheter 10, including tip assembly 14, may be navigated to a site in the body where a medical procedure, such as an atrial mapping, pacing and/or lesion formation are to occur. Distal end portion 30 may extend, for example, into a heart chamber of a patient, and the electrodes 16 energized using an electrical burst or pulse.

The electrical energy may be delivered through electrode rings (e.g., made of platinum) located at the tip assembly 14 of the tissue therapy catheter 10. The tissue therapy catheter 10 may be electrically connected to the power source via the standard 14 pin connector 22. The tissue therapy catheter 10 may have approximately 10 millimeter distance from the distal tip to the first platinum ring. There may be approximately one millimeter spacing between the first platinum ring and the second, and so forth. Wire (e.g., 36 gauge copper wire) may be used to connect the platinum rings to the 14 pin connector.

To improve the efficiency and efficacy of the procedure, each of the electrodes may be independently and/or selectively activated and/or energized based on electrode-tissue contact, and more specifically by electrode-tissue electrical coupling. In an example, the electrode-tissue coupling technology may be implemented using an electrical coupling index "ECI", such as that described in co-owned, co-pending U.S. Patent Publication No. 2009/0163904 titled "System and method for assessing coupling between an electrode and tissue" of Miller, et al., hereby incorporated by reference as though fully set forth herein. Miller describes systems and methods for assessing a degree of coupling between an electrode and tissue in a body. Values for components of a complex impedance (e.g., resistance and reactance or impedance magnitude and phase angle) between the electrode and the tissue are obtained, and a coupling index is calculated that that is indicative of a degree of coupling between the electrode and the tissue.

Figure 5:
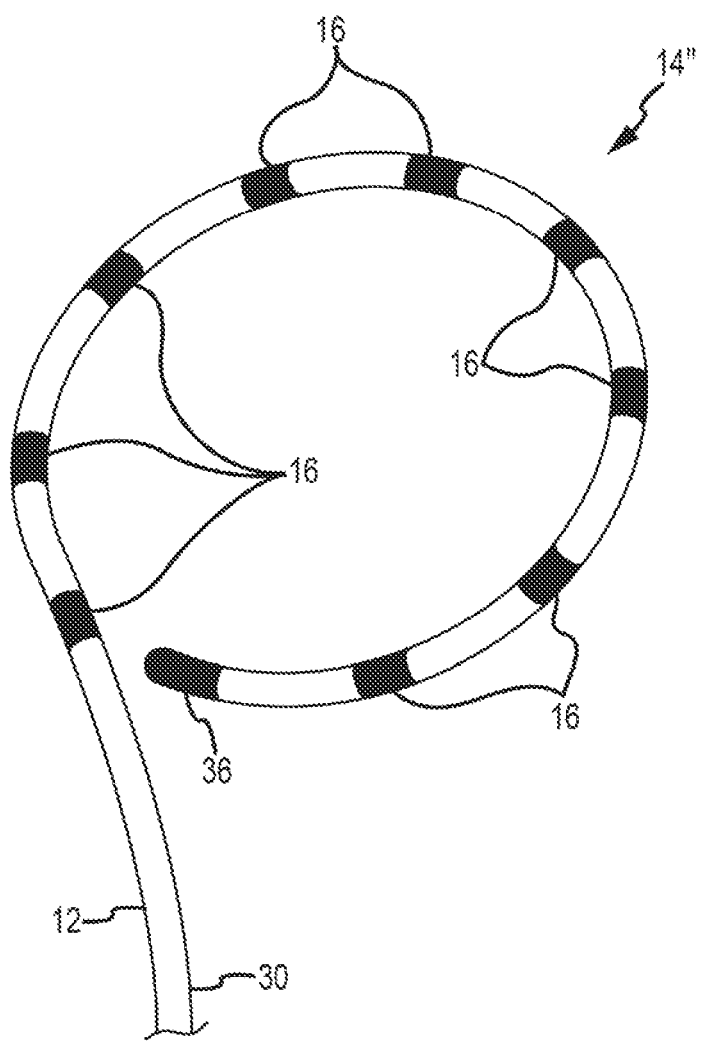
FIG. 5 is a magnified isometric view of a distal end of a tissue therapy catheter showing a tip assembly of the catheter and the electrodes in more detail.

FIG. 5 is a magnified isometric view of a distal end of a tissue therapy catheter (e.g., tissue therapy catheter 10 shown in FIG. 1, or the related embodiments) showing a tip assembly 14" of the catheter and the electrodes 16 in more detail. Tip assembly 14" may be more rigid than flexible tubing 12, e.g., in order to maintain a predetermined shape. In that regard, tip assembly 14" may have any suitable, shape, e.g., as provided at least in part using a forming wire, such as a nitinol wire. Although the tip assembly 14" may be shown and described herein having a generally helical or cylindrical shape, other configurations may also be used. For example, an in-line configuration (not shown) may be used, where the tip assembly 14" is straight and generally linear along a, longitudinal axis. In any event, tip assembly 14" may be a generally flexible member that can be flexed, and can bend or deflect along its axial length, for example, to different operating positions.

Tip assembly 14" may also include multiple electrode elements, such as ring electrodes 16 spaced from one another by dielectric materials as is known in the art. Tip assembly 14" may also include a tip electrode 36, and a temperature sensor (not shown). The tip electrode 36 may be connected to the end of tip assembly 14". Band electrodes 16 are, in one embodiment, attached to an outer surface of tip assembly 14". Lead wires extend to one or more of the band electrodes 16 and/or the tip electrode 36 (and the temperature sensor and any other components, as necessary) as described in more detail with reference to the embodiments shown in FIGS. 9A-D, and to electrical connector 22 (shown in FIG. 1) so that the electrodes may be energized by a power source (not shown), and so that data may be provided for the user.

In an exemplary embodiment, the band electrodes 16 are 5-7 Fr ring-shaped band electrodes, for example, 2 mm in length, and spaced from the tip electrode 36 by a predetermined distance of 2 mm. The tip electrode 36 may be, for example an 8 Fr hemispherical-shaped tip electrode that may be 2 mm in length. In other embodiments, other sizes of electrodes 16, 36 may be utilized, including but not limited to 4 mm or 8 mm electrodes. In the exemplary embodiment, the electrodes 16, 36 are fabricated from 90% platinum and 10% iridium, or other materials known in the art such that the electrodes are viewable under fluoroscopic exposure. Each of the electrodes 16, 36 may also include multiple electrode elements. Of course, the electrodes can comprise a single, continuous electrode or segment of conductive material.

Tip assembly 14" is shown in FIG. 5 having nine band electrodes 16 and one tip electrode 36. Of course, more or fewer electrodes may be implemented. For example, tip assembly 14" may be particularly well suited for lesion formation procedures where electrodes 16 and 36 are energized to conduct current at the site of an abnormal electrical pathway in the body. DC electrical energy may therefore be applied to biological tissue in proximity to tip assembly 14". Therapy procedures are typically used, for example, within the interior chambers of the heart. Electrodes 16 and 36 may also be operated to record intracardiac signals and to provide pacing signals. In one embodiment, separate electrodes may be provided for lesion formation and mapping. In another embodiment, the same electrodes may be implemented for either procedure.

In another embodiment, larger electrodes may be constructed from multiple smaller electrodes. Larger electrodes, if well positioned, can provide lines of block and make, for example, PV isolation simpler and faster. Adjacent electrodes may be activated in sequence to successively rotate the focus of the electrical field around the circumference of a PV. The timing may be electronically controlled to ramp one up as the adjacent one is nearing its mid-high amplitude and thus reduce edge effect field intensities as well. By keeping each electrode's electrical energy delivery short, the benefit of more efficient energy delivery (less loss to conduction or convection) may be maintained.

It is also noted that the surface of the electrodes may be treated, e.g., to increase the surface area and/or to reduce impedance. For example, the surface of the electrodes may be treated so that the "center" of the electrodes has a lower impedance than the "edges" to reduce edge effects and reduce the occurrence of sparks.

In other embodiments, high-conductivity metal may be used in construction of the wires. For example, a larger gauge wire may be used to accommodate a higher current. The catheter shaft 12 itself may also be manufactured of suitable materials which are optimized for the delivery of high voltages to the electrodes 16.

As already mentioned above, a ground needs to be provided in a current path in order to conduct the DC current and create the electrical field. This may be accomplished using a skin patch, but may result in undesirable movement of the patient's body in response to current pulses. Alternatively, a second catheter may be positioned in the patient's body sufficiently close to the electrodes 16 on the first catheter, to provide a return current path. In still other embodiments, an indifferent electrode or electrodes, such as indifferent electrode 40 (FIG. 1) and/or indifferent electrode 40" (FIG. 2), may be implemented.

Figure 6:
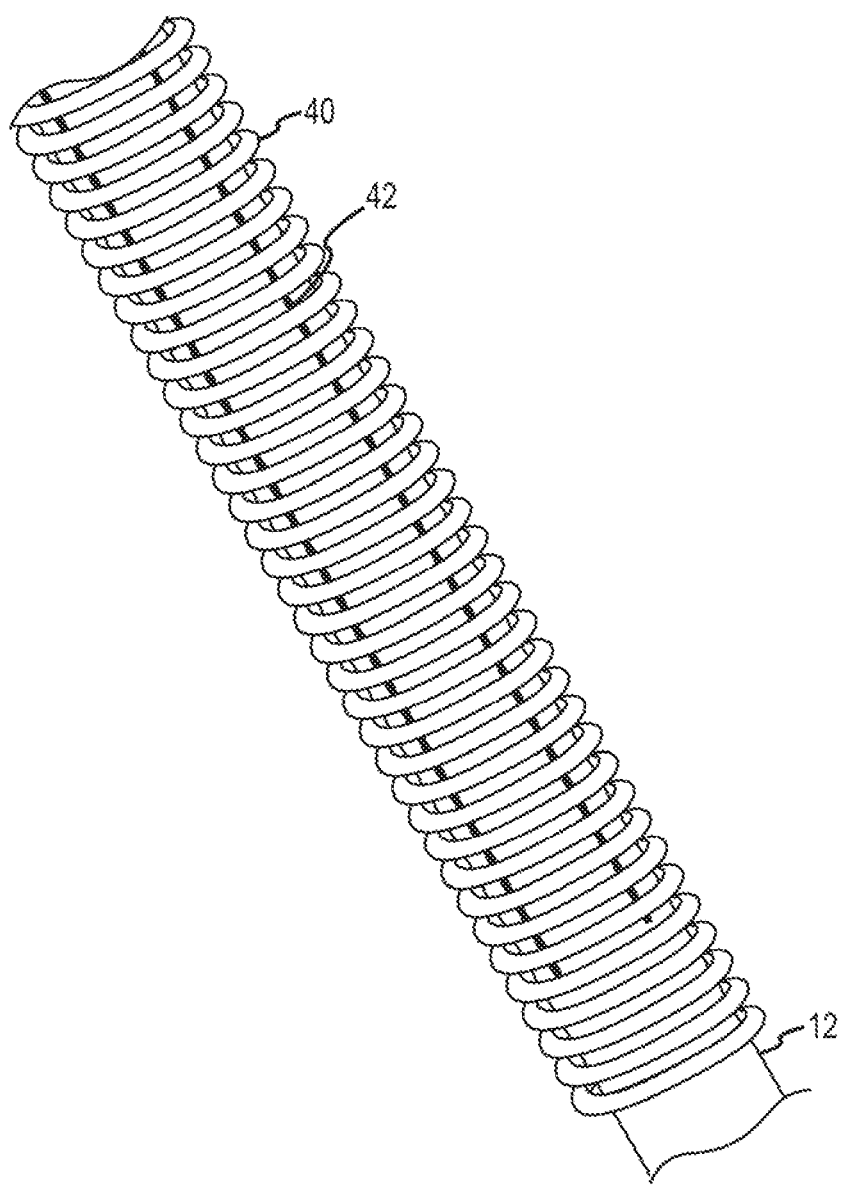
FIG. 6 is a magnified view of a coil provided on the shaft of a tissue therapy catheter.

FIG. 6 is a magnified view of an indifferent electrode 40 (e.g., a conductive coil) provided on the shaft 12 of the catheter 10. Providing a coil on the outside of the shaft 12 may be clinically beneficial because it eliminates the need for a skin patch, and decreases the number of catheters that the physician must use in a procedure.

The coil may be provided anywhere along the length of the shaft 12, and the coil can be any suitable length, provided that it can withstand the energy delivered. That is it may be undesirable for the coil to be too short, due to the heat generated increasing as the length decreases. In one example, the coil may be about 2.4 inches, although longer or shorter coils may also be implemented. The coil may be provided on the outside of the shaft 12, and/or separately positioned within a patient via placing the catheter inside a sheath 2 (shown in FIGS. 2 and 3) such that the sheath 2 covers at least a portion of the shaft 12. In one example, several individual wire lumens run inside the wall of the sheath to form the coil.

At very high energy levels (e.g., about 200 Joules), the coils of the indifferent electrode may melt. To reduce resistance in the coils, and thus the associated heat, a shunt or "shorting wire" 42 may be positioned underneath the coil. The shorting wire may be a flattened platinum wire that shorts some or all of the individual windings of the indifferent electrode together. Multiple shorting wires may also be provided and may not extend the entire length of the coil. For example and in at least one embodiment, four shorting wires may be spaced equidistantly about the circumference of the shaft/coil. The multiple wires may function separately and/or be selectively connected together based on the energy level being utilized for a particular procedure.

Once the coil is shorted so that it is no longer an inductor, there exists the possibility for other flexible electrode configurations, such as the use of braid electrodes, conductive polymer electrodes, and flexible electrodes. A flexible electrode includes an electrode with a tongue and groove connecting adjacent portions. One embodiment of a flexible electrode is disclosed in U.S. patent application Ser. No. 11/853,759, entitled "Ablation Catheter with Flexible Tip and Methods of Making the Same," which is hereby incorporated by reference as though fully set forth herein. Another embodiment of a flexible electrode is disclosed in U.S. patent application Ser. No. 12/436,977, entitled "Irrigated Ablation Catheter with Multiple Segmented Ablation Electrodes," which is hereby incorporated by reference as though fully set forth herein. This configuration allows some degree of flexibility, but the electrode is not an inductor since, these tongue and grooves may short the electrode together.

Figure 7:
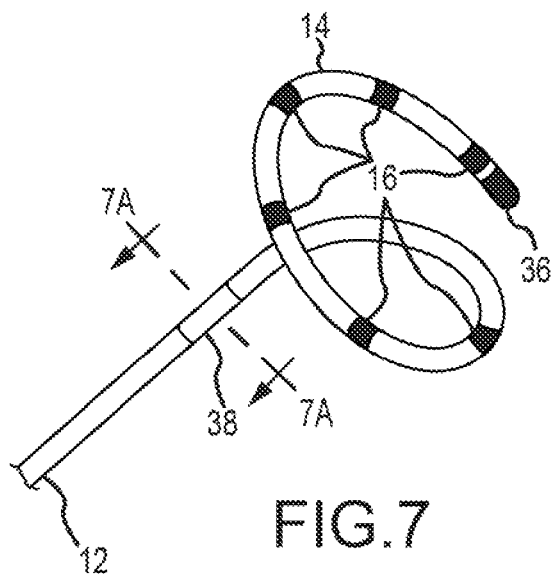
FIG. 7 is an isometric view of the distal end of a tissue therapy catheter, further illustrating a movable shield.
Figure 7A:
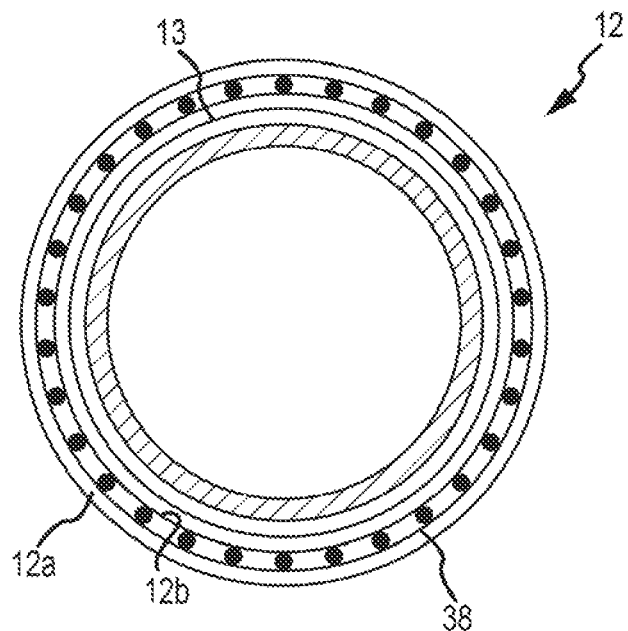
FIG. 7A is a cross-sectional view of the shaft of the catheter and the shield of FIG. 7, taken through lines 7A-7A in FIG. 7.

FIG. 7 shows isometric views of the distal end of the tissue therapy catheter 10, further illustrating a movable shield 38. The shield 38 may be operated to cover one or more of the electrodes 16 and/or a portion or all of an indifferent electrode during use. FIG. 7A is a cross-sectional view of the shaft 12 of the tissue therapy catheter 10 and the shield taken along lines 7A-7A in FIG. 7. In the embodiment shown, the shield 38 may be moveable in an outer catheter lumen formed between catheter walls 12a and 12b, which may be provided over an inner catheter 13 and including the electrodes 16. The shield may function to control placement, direction and/or magnitude of the electric field created by the tissue therapy electrodes. Other embodiments are also contemplated, such as a shield having one or more openings ("windows") formed therein. The size of the windows may also be adjustable for different procedures.

Figure 8B:
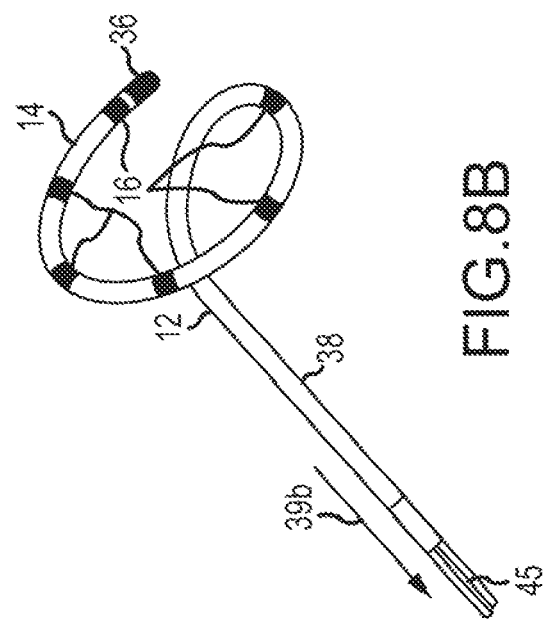
FIGS. 8A-B are isometric views of the distal end of the catheter as shown in FIG. 7 illustrating movement of the shield.
Figure 8A:
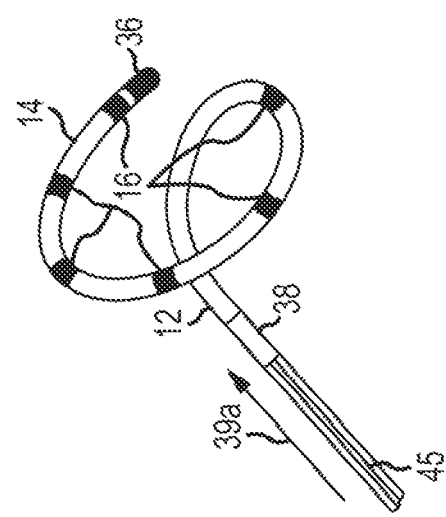
Figure 8D:
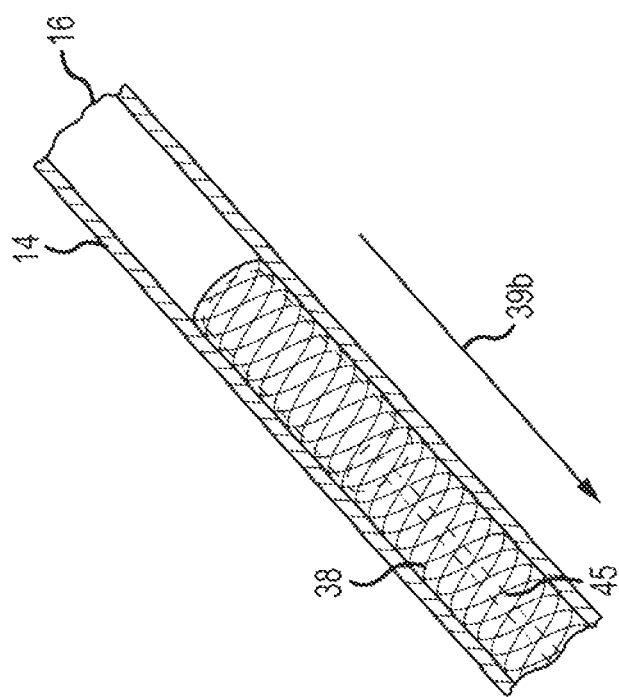
FIGS. 8C-D are magnified isometric views of a distal portion of the catheter as shown in FIG. 7 further illustrating movement of the shield.
Figure 8C:
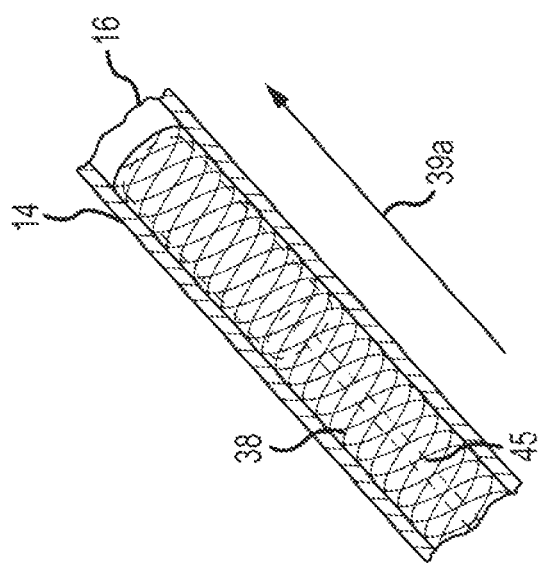
Figure 9A:
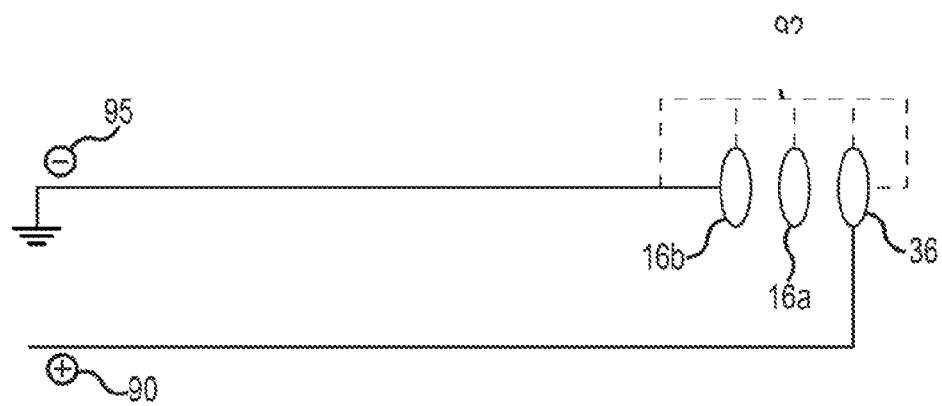
FIGS. 9A-E are exemplary high-level circuit diagrams illustrating different current paths through one or more electrodes in a tissue therapy catheter.
Figure 9B:
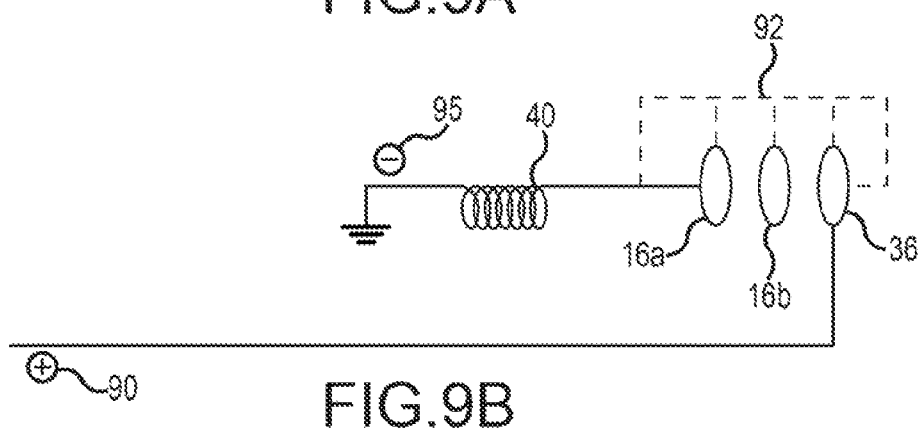
Figure 9C:
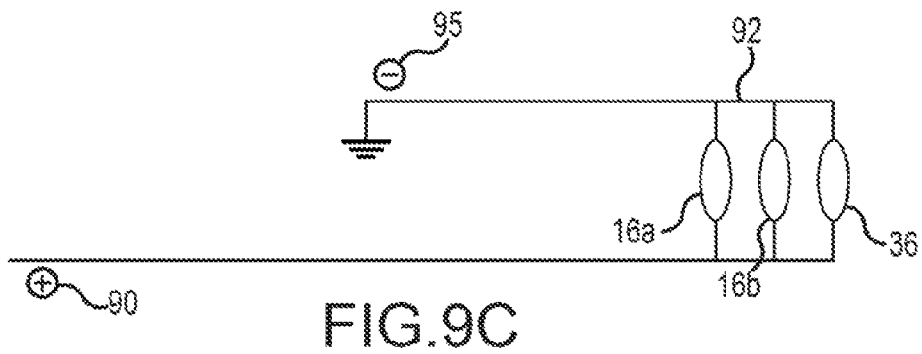
Figure 9D:
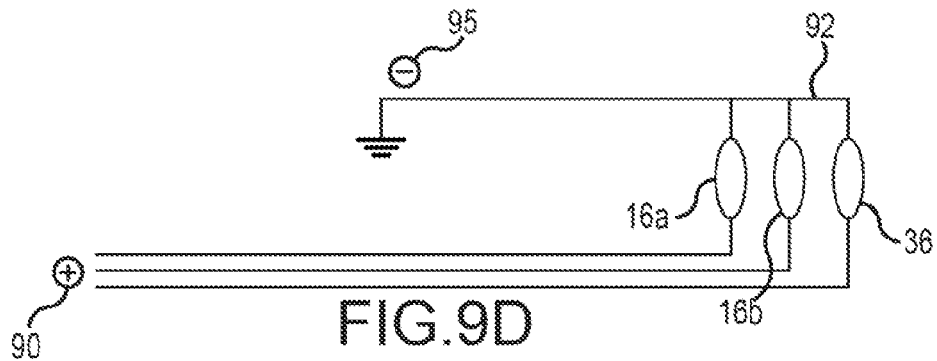
Figure 9E:
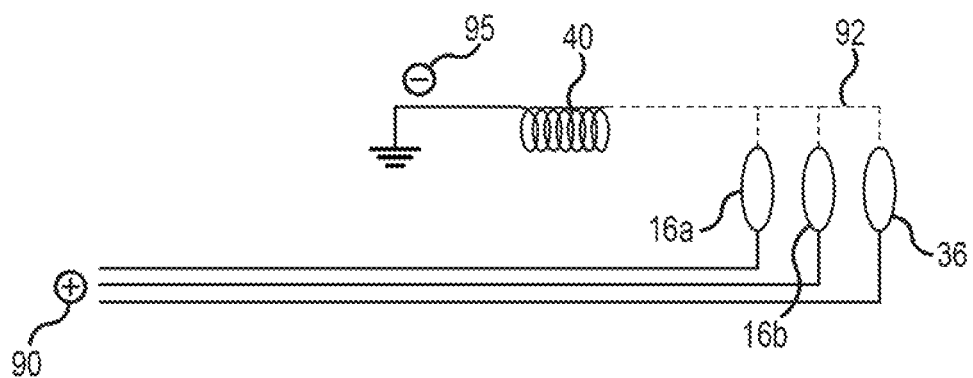

FIGS. 8A-B are isometric views of the distal end of the catheter 10 as shown in FIG. 7 illustrating movement of the shield 38. FIGS. 8C-D are magnified isometric views of a distal portion of the catheter 10 as shown in FIG. 7 further illustrating movement of the shield shown in FIG. 7, further illustrating movement of the shield 38. For example, the shield may be moved in the direction illustrated by arrow 39a shown in FIG. 7A to cover one or more of the electrodes 16 in the tip assembly 14. Likewise, the shield 38 may be moved in the direction illustrated by arrow 39b shown in FIG. 7B to uncover one or more of the electrodes 16 in the tip assembly 14.

A control mechanism may be operable by the user to selectively position the shield 38 at various locations on an as-needed or as-desired basis. In an exemplary embodiment, the shield 38 may be positioned by the user from the proximal end 28 of the flexible tubing 12, e.g., at connector 18 when implemented as a handle. In an exemplary embodiment, the control mechanism includes a tether 45 (e.g., a wire) connected on one end to the shield 38, and provided through the lumen of the shaft 12 outside of the patient's body. The tether 45 may be sufficiently stiff so as to enable pushing and pulling of the shield 38.

Another manually operated control mechanism may also include a reel that can be rotated to push the tether 45 in a first direction toward the distal end 30 of the catheter 10. The reel can also be rotated the opposite direction to pull the tether 45 in a second direction toward the proximal end 28 of the catheter 10. Automated control mechanisms may also be provided, including, but not limited to, motor-driven devices which respond to signals from a computer or other electronic device. Although the control mechanism may be illustrated as a tether 45, other control mechanisms are also contemplated.

Before continuing, it should be noted that the catheter 10 may be implemented as an irrigated catheter. In an exemplary embodiment, the luer device 20 shown in FIG. 1 may be used to open or close a flow path so that fluid may be passed through Y-connector 18 and tubing 12 to tip assembly 14, for example, when the catheter 10 is also used for irrigation purposes. Tip assembly 14 may include one or more openings or irrigation ports (not shown) for passage of fluid from within tubing 12 to an exterior of tip assembly 14 when located in the body of a patient. Inner tube 24 forms fluid lumen which connects directly to a plurality of openings that form irrigation ports, e.g., for saline irrigation. Tubing 24 may be formed, for example, by a braided polyimide tube that maintains the flow path through lumen in all orientations of tip assembly 14, without compromising the flexibility of tubing 12.

In one embodiment of an irrigated catheter, the tip electrode and/or other locations in the tip assembly 14 may be formed with a plurality of openings, e.g., between two or more of the electrodes 16. A central lumen may be in fluid communication with luer 20 (shown in FIG. 1) on one end, and with the ports at the other end. Thus, a conductive fluid or gel may be injected through the inner tube 24 and secreted from the ports to form a current path and facilitate conduction of an electrical current between the electrodes 16 (e.g., just at or immediately preceding therapy delivery). In another embodiment, the surface of the catheter shaft 12 itself may also be treated to increase the dielectric properties, e.g., to enhance formation of a current path upon delivery of DC current to the electrodes.

FIGS. 9A-E are exemplary high-level circuit diagrams illustrating different current paths through one or more electrodes. In the example shown in FIG. 9A, current may be delivered from the positive electrode 90 to the tip electrode 36. The current path 92 may be completed through the other electrodes 16a and 16b via the tissue, blood, and/or a conductive fluid or gel secreted between the electrodes, to ground 95. In the example shown in FIG. 9B, current may be delivered from the positive electrode 90 to the tip electrode 36. The current path 92 may be completed through the other electrodes 16a and 16b via the tissue, blood, and/or a conductive fluid or gel secreted between the electrodes, to the indifferent electrode 40 which serves as ground 95. In the example shown in FIG. 9C, current may be delivered through the current path 92 from the positive electrode 90 to each of the electrodes 16a, 16b, and the tip electrode 36 wired in parallel. In the example shown in FIG. 9D, current may be delivered through the current path 92 from the positive electrode 90 to each of the electrodes 16a, 16b, and the tip electrode 36 wired in series. In the example shown in FIG. 9E, current may be delivered through the current path 92 from the positive electrode 90 to a subset or each of the electrodes 16a, 16b, and/or the tip electrode 36. The current path 92 may be completed via the tissue, blood, and/or a conductive fluid or gel secreted between the electrodes, to the indifferent electrode 40 which may serve as a conduit to ground 95.

These current paths can create an electrical field in or near (e.g., adjacent) tissue to be diagnosed and/or treated. In an embodiment, the energy application may last between about 0.02 to 2 seconds in duration and include a multiphasic waveform substantially higher in frequency than that used for skeletal muscle and nerve stimulation (for example, 1 kHz to 10 MHz). The energy application may optionally be timed to the cardiac cycle to enhance location accuracy. In any event, in at least one embodiment, the waveform should ideally avoid abrupt onset or offset changes in amplitude to reduce muscle and nerve stimulation, using instead a wave envelope with graded onset and offset.

Electrodes with micro patterned edges may be created for example with laser machining to effectively create series resistance while still in proximity to the central electrode or electrodes of highest potential but reducing the current and voltage at the outermost aspects of the electrode. A preferred embodiment might incorporate a micro patterned or feathered tip electrode (e.g., approximately 4 mm at the tip). While in some embodiments a DC energy source may be used, in at least one embodiment an RF frequency energy source (such as a 500 kHz generator used for ablation) may be enveloped in square pulses, or in trapezoidal pulses with, for example, a total duration of about 200 ms, a duty cycle of about 50%, and a rise and fall time of about 20 ms. An embodiment may also present the option for a user to trigger these square pulses based on surface ECG or catheter EGM.

In one embodiment, abbreviated lesion formation may be implemented to manage cardiac arrhythmias. The term "abbreviated tissue therapy" is used herein to refer to any method of delivering electrical energy to effect a permanent change in cardiac conduction that is substantially shorter in duration than the roughly 10-40 seconds used when about 20-40 watts of about 500 kHz RF energy is used to devitalize the tissue. Abbreviated tissue therapy may be effected, e.g., by controlling different waveforms/timing, amplitude/energy of the electrical current being utilized.

By way of example, it may be advantageous to use a balanced application of current (e.g., AC or multi-phasic) so as to keep residual polarization of electrode surfaces to a minimum and thereby permit electrogram signal amplification without saturation during and immediately after lesion formation. It may also be advantageous to keep the application of electric energy short so as to not transfer substantial heat energy to adjacent, healthy tissue by conduction or convection. If may also be advantageous to use short applications of energy timed, for instance, to a specific phase of the cardiac cycle where cardiac motion can be effectively "frozen" or when stable catheter positioning is difficult and the desired location can be achieved only briefly.

Also by way of example, 20-200 Joules pulse waveforms may be delivered at the catheter electrodes to produce the desired effects on cardiac conduction. Traditional RF energies are not greatly dissimilar (20 watts over 15 seconds is 300 J) and may be more wasteful, heating blood and raising the temperature of adjacent tissue. The duration of the electrical burst or pulse waveforms may be about 10-20 ms, which implies a mean voltage on the order of about 300-500 V across a load of 100 ohms. Less voltage may be used with longer durations. This translates to a mean RMS voltage of about 50 VAC. Higher voltages of sufficient duration may induce arcing which results in explosive tissue and/or steam "pops," as water and blood breaks down into ions. Higher voltage may also require more extensive catheter and connector insulation, which may be provided in at least some embodiments herein.

Briefer applications of effective amounts of energy imply greater amplitudes and higher field intensity near the electrode. To a certain extent this can be counteracted by a larger surface area electrode and/or by reducing the field intensity near the electrode edges, such as by incorporating series resistance to electrode segments at the border. This can be achieved by electronic or metallurgical or surface property modifications of traditional electrodes. Excessive electrode size is counterproductive to delivery of targeted energy on compact catheters.

Before continuing, it should also be noted that instrumentation may also be provided for use with the catheter 10 and electrodes 16 described herein. Such instrumentation may, for example, be used with suitable sensors and measurements to display or otherwise output parameters such as total energy being delivered, energy being delivered to each electrode, peak voltage, peak current, duration of current delivery, polarity, and so forth, to name only a few examples. Algorithms implemented in software or other program code may also be implemented to "predict" lesion formation (e.g., depth and/or volume) based on parameter measurements. Likewise, algorithms may also be implemented in software or other program code to assist the user in identifying damaged catheters prior to use based on measurement of these parameters (e.g., exceeding a predetermined safe level of current delivery).

FIG. 10 shows a high-level-block diagram of exemplary control circuitry 100 for delivering an electrical pulse across one or more electrodes 101 in a tissue therapy catheter to create an electrical field for tissue therapy procedures. An electrical delivery device 110 may be provided to house the electronic circuitry external to the patient's body during a procedure. The device 110 may include a power supply 111, such as a high voltage power supply (HVPS), and an electric pulse generator 112. Electric pulse generator 112 may include a truncated silicon controlled rectifier (SCR), SCR triggering circuitry, and current and voltage dividers.

A truncated SCR may be used as a safety precaution to prevent unnecessary energy delivery to the patient. A current divider helps ensure that most of the energy is delivered through the heart, while the voltage divider may be used as a method of stepping down high voltage in order to protect the computer monitoring system. In one embodiment, LabVIEW software or other suitable program code 113 may be implemented to control the electronic circuitry, thereby creating the desired pulse widths, number of pulses, and frequency of energy delivery. The control software 113 may also cause a display to output voltage, output current, and energy delivered over the heart during the procedure, e.g., via a sensing function. Circuitry control may be accomplished with microcontrollers and embedded software to increase efficiency.

In one embodiment, the high voltage power supply (HVPS) 111 may be used to charge capacitors which then produce electric current. A system of relays and SCRs safely contain the energy until delivery may be required. A triggering method may be used on the output SCR. The software controls a phototransistor optocoupler, which in turn triggers the corresponding SCR. The optocoupler or other switching devices 114 isolate the high voltage (through the SCR) from an external computer monitoring system. An SCR in the open position allows no current through, therefore isolating the heart. A second SCR trigger may be used in the truncated circuit path. The truncated path provides a bypass around the patient to discharge electricity when not needed, or if the procedure is aborted. For example, the truncated SCR may be triggered in order to control pulse width at the heart. Since a closed SCR remains conductive until the forward current drops below the a threshold, closing the truncated SCR at the end of the desired pulse width discharges the capacitors through the low resistance truncated path, causing the output SCR's forward current to drop sufficiently to cease delivery to the heart.

Voltages of up to 1000 volts of sufficiently short duration may be preferred for electroporation. This requires a high voltage power supply. In at least one embodiment, a Matsusada W series power supply may be used for tissue therapy. Included in this circuitry are switches controlling both the power and interlock, and an emergency shut off. The HVPS 111 may also put out a signal of about 5 volts when it is on and operating within predetermined safety parameters. This may also be recorded and displayed for the user. Voltage and current output may also be displayed and controlled by potentiometers. The circuitry (and associated program code) also provides several layers of isolation for safety. For example, relays are used to individually charge and discharge the capacitors, thereby enabling electrical isolation of the patient from the HVPS.

It should be noted that various embodiments described herein may also be implemented with a catheter and/or a catheter/sheath combo. In addition, the various embodiments are also well-suited for use with EnSite™, Carto™, MediGuide™ and/or other navigation/mapping systems for real-time tracking for minimally-invasive intra-body navigation. With these systems, the 3-D position and orientation of the catheter can be calculated in real time and projected graphically on a display for a user during a medical procedure.

Although various embodiments described herein include a tissue therapy catheter that may be used for various medical procedures such as mapping and/or lesion formation procedures, other uses are also contemplated and will become readily apparent to those having ordinary skill in the medical devices arts after becoming familiar with the teachings herein. Other exemplary uses may include, but are not limited to, tumor or cancer treatment. For example, a catheter with DC electrodes may be used to kill cancerous cell(s) located near the vascular system or elsewhere in a patient's body. Also as already mentioned above, electroporation may be used as a method of drug delivery, introducing drugs directly inside a cell's or cells' cellular membrane(s). Similarly, electroporation may be used for gene therapy.

While the invention has been described in terms of various specific embodiments, those skilled in the art will recognize that the invention can be practiced with modification within the spirit and scope of the claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter device comprising:
    an elongate member comprising at least one ablation electrode;
    a steerable sheath sized and configured to introduce the elongate member inside a patient's body;
    an indifferent coil electrode comprising a plurality of windings on the steerable sheath, wherein the plurality of coil windings are electrically connected by at least one shunt, thereby preventing the plurality of coil windings from acting as an inductor, and wherein the plurality of coil windings and the shunt are thereby configured to allow for a current path of a direct current pulse to be delivered between the at least one ablation electrode and the indifferent electrode to create an electrical field adjacent a tissue; and
    a steering actuator operatively coupled to the steerable sheath for actively deflecting the steerable sheath.

2. The catheter device of claim 1 wherein the steering actuator is operably coupled to a plurality of deflectable elements extending longitudinally along the steerable sheath.

3. The catheter device of claim 1 wherein the direct current pulse is characterized by a variable frequency waveform.

4. The catheter device of claim 1 wherein the direct current pulse is characterized by a variable amplitude waveform.

5. The catheter device of claim 1 wherein the direct current pulse is characterized by a variable duration waveform.

6. The catheter device of claim 1 wherein the elongate member comprises a hoop portion, and wherein the at least one ablation electrode is positioned on the hoop portion.

7. The catheter device of claim 1 wherein a plurality of electrodes that are wired together in series are mounted along the elongate member.

8. The catheter device of claim 7 wherein the plurality of electrodes are electrically connected in series only during delivery of the DC pulse.

9. The catheter device of claim 1 further comprising at least one port formed in the elongate member, the at least one port configured to secrete a conductive material to facilitate formation of a current path.

10. A steerable introducer comprising:
    an elongated body comprising a proximal portion, a distal portion, and a sidewall; the elongated body defining a lumen sized and configured to receive a catheter, and wherein at least one deflectable element is disposed within the sidewall;
    an indifferent coil electrode comprising a plurality of windings positioned on the elongated body and electrically shorted together by a shunt connected to at least a plurality of the coil windings along a length of the indifferent electrode, whereby the coil windings are prevented from acting as an inductor, and wherein the coil windings and the shunt are thereby configured to provide an energy-dispersing electrical ground for a direct current pulse for lesion formation or visualization procedures; and
    a steering mechanism operatively coupled to the proximal portion of the elongated body and to the at least one deflectable element, wherein the steering mechanism is configured to selectably deflect the distal portion of the elongated body.

11. A kit comprising:
    a catheter comprising a proximal end, a distal end with a substantially round shaped tip configured for atraumatic introduction into a heart, and at least one electrode located near the distal end; and
    a sheath comprising a proximal end and a distal end, the sheath defining a lumen sized and configured to receive the catheter, wherein the sheath further comprises an indifferent coil electrode comprising a plurality of coil windings including end coil windings and intermediate coil windings between the end coil windings, wherein the coil windings are configured to provide a ground for a current path from a power source through the at least one electrode, wherein a shunt connects at least a subset of the plurality of coil windings comprising the intermediate coil windings, thereby preventing at least the subset of coil windings from acting as an inductor, and wherein the shunt is configured to distribute electrical energy among at least the subset of coil windings; wherein the sheath further comprises a deflectable element comprising a distal end anchored at or near the distal end of the sheath; and wherein a steering mechanism is operatively coupled to a proximal end of the deflectable element at or near a proximal end of the sheath.

12. The kit of claim 11 wherein the at least one electrode comprises a plurality of electrodes that are configured such that during operation a direct current pulse provides current to each of the plurality of electrodes at substantially the same time.

13. The kit of claim 11 wherein the sheath further comprises an inner layer and an outer layer, and wherein the outer layer comprises a minor lumen disposed therein that slideably houses the deflectable element.

14. The kit of claim 11 wherein the plurality of coil windings are configured to provide a high surface area for dissipating heat created when electrical energy flows through at least a portion of the coil.

15. The kit of claim 11 wherein the plurality of coil windings have a winding pitch configured to provide a high surface area for dissipating heat created when electrical energy flows through at least a portion of the coil.

16. The kit of claim 11 wherein the at least one electrode comprises a segmented electrode.

17. The kit of claim 11 wherein the at least one electrode is coated with a conductive polymer.

18. The kit of claim 11 wherein the at least one electrode is configured to be independently and selectively energized based on electrode-tissue contact and electrical coupling determined with an electrical coupling index calculated using values for components of complex impedance between the at least one electrode and the heart.

19. A kit comprising:
   a catheter comprising a proximal end, a distal end with a substantially round shaped tip configured for atraumatic introduction into a heart, and at least one electrode located near the distal end; and
   a sheath comprising a proximal end and a distal end, the sheath defining a lumen sized and configured to receive the catheter, wherein the sheath further comprises an indifferent coil electrode comprising a plurality of coil windings including end coil windings and intermediate coil windings between the end coil windings, wherein the coil windings are configured to provide a ground for a current path from a power source through the at least one electrode, wherein a shunt connects at least a subset of the plurality of coil windings comprising the intermediate coil windings, and wherein the shunt is configured to distribute electrical energy among at least the subset of coil windings; wherein the sheath further comprises a deflectable element comprising a distal end anchored at or near the distal end of the sheath; and wherein a steering mechanism is operatively coupled to a proximal end of the deflectable element at or near a proximal end of the sheath;
   wherein the at least one electrode comprises a plurality of electrodes, wherein the catheter further comprises an inner catheter wall and an outer catheter wall, and wherein a movable shield configured to selectably cover at least one of the plurality of electrodes is moveably mounted in an outer catheter lumen formed between the inner catheter wall and the outer catheter wall.

20. The kit of claim 19 wherein the movable shield further comprises at least one window formed therein.

21. The kit of claim 19 further comprising a tether connected to the shield and configured to selectably move the shield.

22. The kit of claim 21 further comprising a reel operably connected to the tether.

* * * * *